(12) United States Patent
Stokes et al.

(10) Patent No.: US 11,549,902 B2
(45) Date of Patent: Jan. 10, 2023

(54) DETERMINING A CATION EXCHANGE CAPACITY OF A ROCK SAMPLE

(71) Applicant: CHEVRON U.S.A. INC., San Ramon, CA (US)

(72) Inventors: Martha Rebecca Stokes, Reston, VA (US); Zheng Yang, Houston, TX (US); Prince E. Ezebuiro, Houston, TX (US); Timothy B. Fischer, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 82 days.

(21) Appl. No.: 16/999,242

(22) Filed: Aug. 21, 2020

(65) Prior Publication Data

US 2021/0318259 A1  Oct. 14, 2021

Related U.S. Application Data

(60) Provisional application No. 62/891,060, filed on Aug. 23, 2019.

(51) Int. Cl.

| G01N 27/22 | (2006.01) |
| G01N 33/24 | (2006.01) |
| E21B 49/00 | (2006.01) |
| E21B 49/02 | (2006.01) |

(52) U.S. Cl.
CPC ......... *G01N 27/221* (2013.01); *E21B 49/005* (2013.01); *G01N 27/223* (2013.01); *G01N 33/246* (2013.01); *E21B 49/02* (2013.01)

(58) Field of Classification Search
CPC .. G01N 27/221; G01N 27/223; G01N 33/246; E21B 49/005; E21B 49/02

USPC ......................................................... 324/376
See application file for complete search history.

(56) References Cited

U.S. PATENT DOCUMENTS

| 2016/0097876 A1* | 4/2016 | Freed ....................... G01V 3/30 703/2 |
| 2018/0120468 A1* | 5/2018 | Seleznev .................. G01V 3/20 |

OTHER PUBLICATIONS

Garrouch, Ali A.; "Predicting the Cation Exchange Capacity of Reservoir Rocks from Complex Dielectric Permittivity Measurements"; 2018 Society of Exploration Geophysics, pp. MR1-MR14.
(Continued)

*Primary Examiner* — Farhana A Hoque

(57) ABSTRACT

Provided herein are various embodiments of determining a cation exchange capacity of a rock sample. One embodiment of a method of determining a cation exchange capacity of a rock sample comprises equilibrating the rock sample to a relative humidity, performing a dielectric permittivity measurement on the rock sample at the relative humidity, and determining a cation exchange capacity of the rock sample based on the dielectric permittivity measurement. One embodiment of a method of determining a cation exchange capacity of a rock sample comprises receiving a dielectric permittivity measurement on the rock sample, and determining a cation exchange capacity for the rock sample based on the dielectric permittivity measurement of the rock sample and a relationship between cation exchange capacity and dielectric permittivity measurements for mineral mixtures corresponding to a range of cation exchange capacity values.

18 Claims, 14 Drawing Sheets

(56) References Cited

OTHER PUBLICATIONS

Leung, P.K., et al.; "Dielectric Constant Measurements: A New, Rapid Method to Characterize Shale at the Wellsite"; IADC/SPE 23887, Feb. 1992, pp. 401-408.

Bardon, C.; "Recommandations pour la détermination expérimentale de la capacité d'échange de cations des milieux argileux," (Abstract), (1983), Rev. Inst. Fr. Pét., vol. 38, No. 5, pp. 621-626, doi: 10.2516/ogst:1983037.

Chung, Frank H.; "Quantitative Interpretation of X-ray Diffraction Patterns of Mixtures. I. Matrix-Flushing Method for Quantitative Multicomponent Analysis"; (1974), J. Appl. Cryst., vol. 7, No. 6, pp. 519-525.

Omotoso, Oladipo, et al.; Some Successful Approaches to Quantitative Mineral Analysis as Revealed by the 3rd Reynolds Cup Contest; (2006), Clays and Clay Minerals, vol. 54, No. 6, pp. 748-760.

Srodon, Jan, et al.; "Quantitative X-Ray Diffraction Analysis of Clay-Bearing Rocks from Random Preparations"; (2001), Clays and Clay Minerals, vol. 49, No. 6, pp. 514-528.

Stokes, M. Rebecca, et al.; "A New CEC-Measurement Proxy Using High-Frequency Dielectric Analysis of Crushed Rock"; (2020), Petrophysics, vol. 61, No. 2, pp. 179-188, 9 Figs., 1 Table.

Stokes, M. Rebecca, et al.; "A New CEC Measurement Proxy Using High-Frequency Dielectric Analysis of Crushed Rock"; (2019), SCA2019-032, 9 pages.

\* cited by examiner

DETERMINING A CATION EXCHANGE CAPACITY OF A ROCK SAMPLE

CROSS REFERENCES TO RELATED APPLICATIONS

This application claims the benefit of priority to 62/891,060 filed Aug. 23, 2019, which is incorporated by reference in its entirety.

STATEMENT REGARDING FEDERALLY SPONSORED RESEARCH OR DEVELOPMENT

Not applicable.

TECHNICAL FIELD

The present disclosure relates to determining a cation exchange capacity of a rock sample.

BACKGROUND

Cation exchange capacity (CEC) is loosely related to the surface charge of a material and it is the measure of the ability to reversibly adsorb cations. Cation exchange capacity is used across many geoscience and engineering fields to characterize clays. For example, cation exchange capacity is a data type commonly referenced in the oil and gas industry as it holds critical information about the swelling potential of a rock, which is an important component in well planning and production modeling. Quantification of clay types and their swelling behavior may be used for drilling and completions planning, borehole instability mitigation, enhanced oil recovery (EOR) planning, and predicting changes in production due to effects from clay swelling. Each of these aspects of hydrocarbon production may be significantly impacted if the rocks of interest are not properly characterized with respect to the clays. However, measuring the cation exchange capacity of a rock sample is typically laborious. For example, depending on the methodology used, measuring the cation exchange capacity may involve saturation and extraction steps, the use of multiple chemicals, titration, and spectroscopic analysis.

A need exists in the art for a simplified manner of determining the cation exchange capacity of a rock sample.

SUMMARY

Provided herein are various embodiments of determining a cation exchange capacity of a rock sample.

One embodiment of a method of determining a cation exchange capacity of a rock sample comprises equilibrating the rock sample to a relative humidity, performing a dielectric permittivity measurement on the rock sample at the relative humidity, and determining a cation exchange capacity of the rock sample based on the dielectric permittivity measurement.

One embodiment of a method of determining a cation exchange capacity of a rock sample comprises receiving a dielectric permittivity measurement on the rock sample, and determining a cation exchange capacity for the rock sample based on the dielectric permittivity measurement of the rock sample and a relationship between cation exchange capacity and dielectric permittivity measurements for mineral mixtures corresponding to a range of cation exchange capacity values.

DESCRIPTION OF THE DRAWINGS

In FIG. 1B, the slope of the curves defines a non-linear relationship between CEC and permittivity as a function of relative humidity (RH). The non-linear relationship is predictable. In FIG. 1B, Slope vs. RH can be correlated by 3 separate best fit lines assigned to low, mid, and high RH conditions. Numerous fitting equations were attempted, including power decay and exponential decay equations.

FIG. 4 also illustrates an example of the typical range observed at low frequencies between the 5 repeated dielectric analyses. Errors based on this are reported in FIG. 5.

Figure 1A:
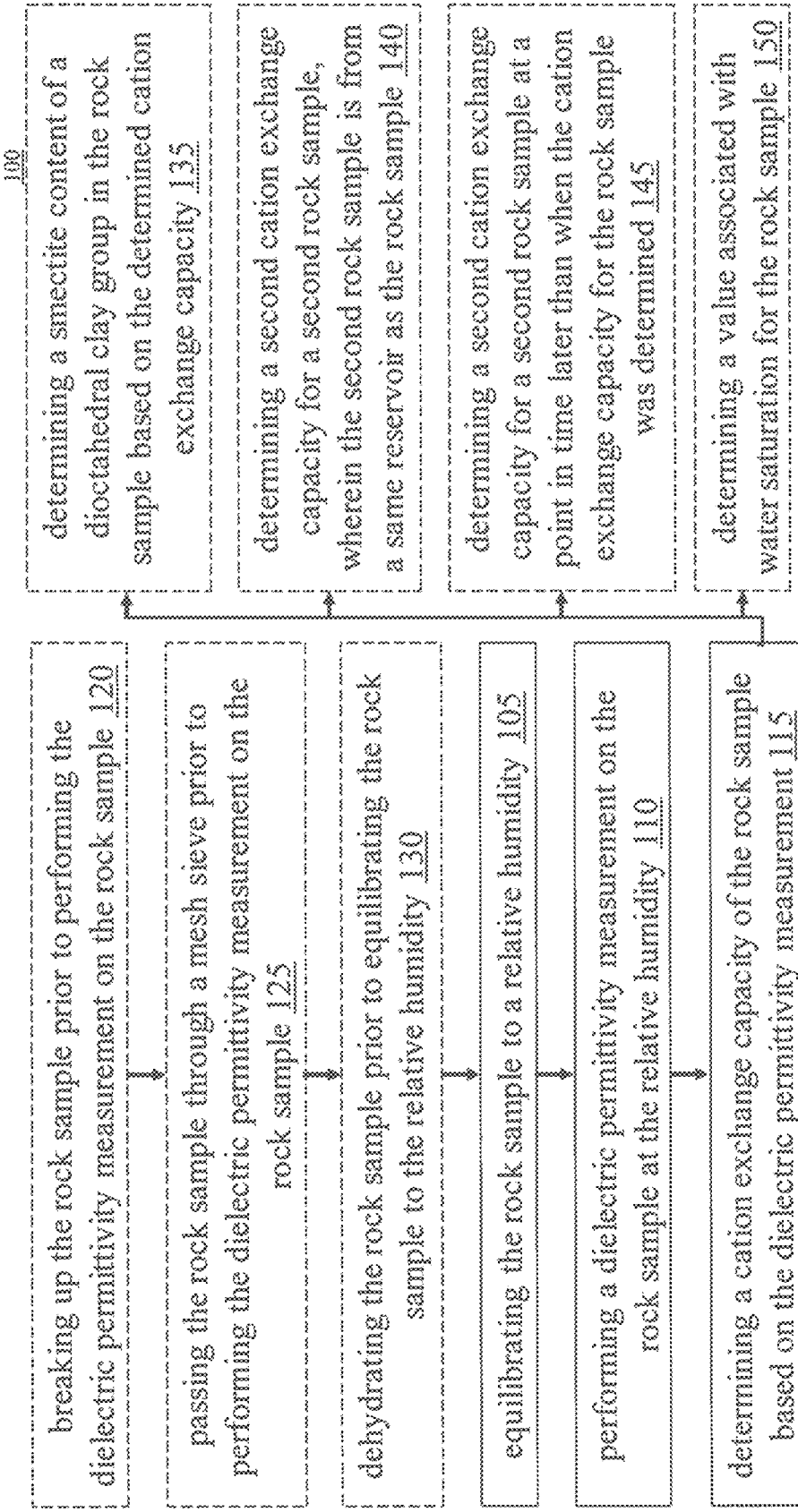
FIG. 1A illustrates a flowchart of one embodiment of a method of determining a cation exchange capacity of a rock sample consistent with the present disclosure.
Figure 1B:
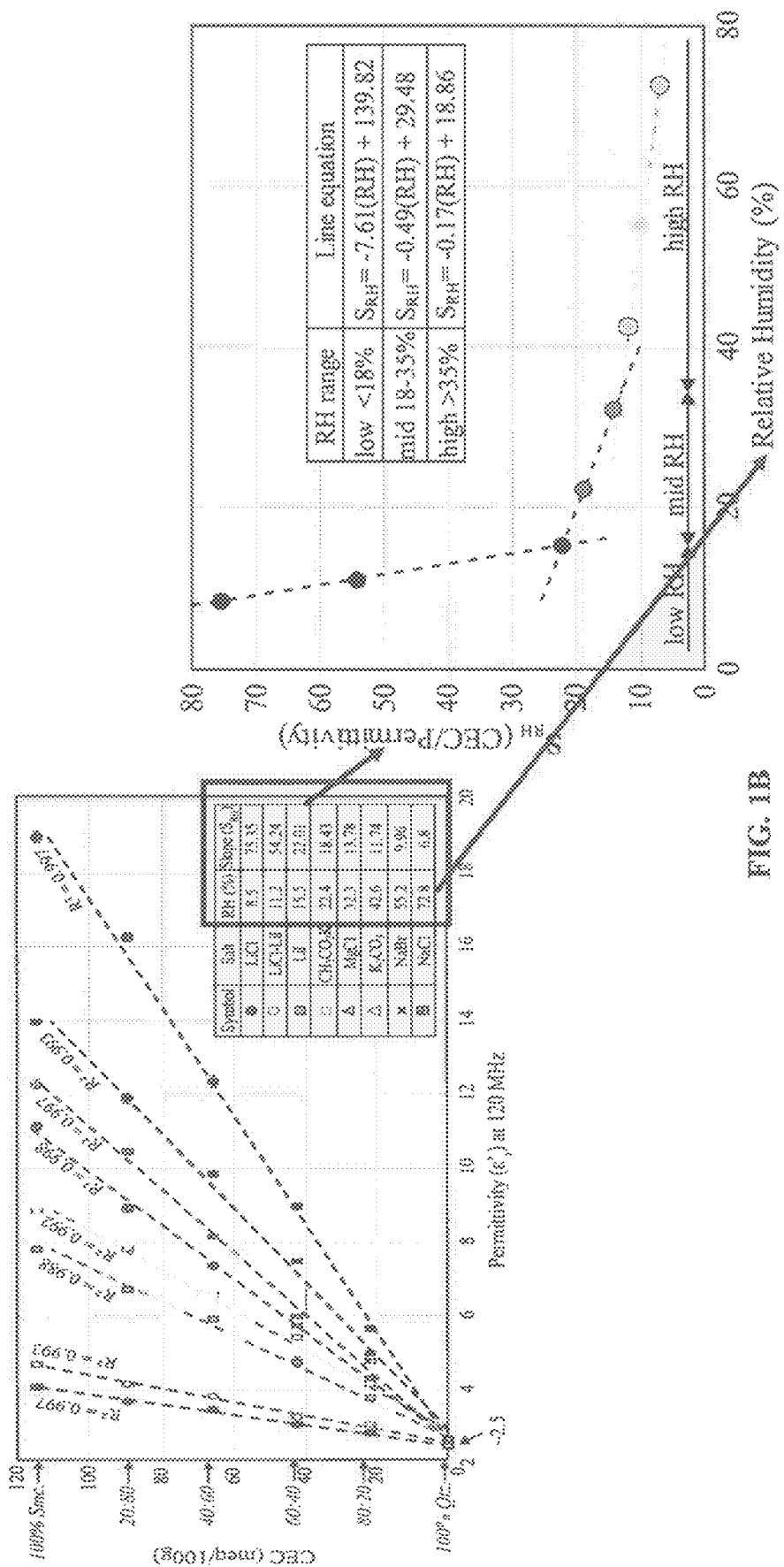
FIG. 1B illustrates one embodiment of equation generation.
Figure 1C:
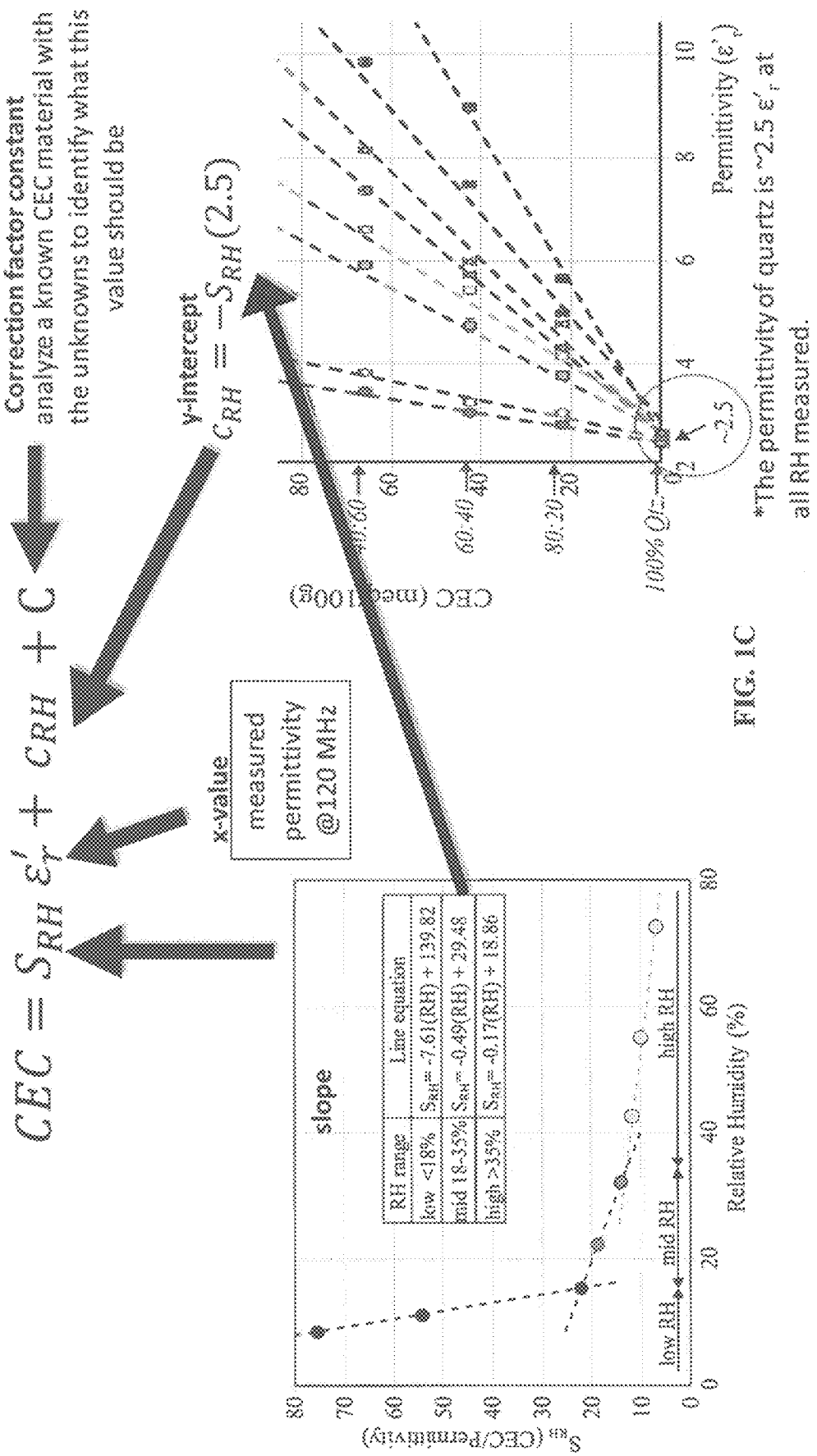
FIG. 1C illustrates one embodiment of calculating CEC from permittivity.

Reference will now be made in detail to various embodiments, where like reference numerals designate corresponding parts throughout the several views. In the following detailed description, numerous specific details are set forth in order to provide a thorough understanding of the present disclosure and the embodiments described herein. However, embodiments described herein may be practiced without these specific details. In other instances, well-known methods, procedures, components, and mechanical apparatuses have not been described in detail so as not to unnecessarily obscure aspects of the embodiments.

DETAILED DESCRIPTION

TERMINOLOGY: The following terms will be used throughout the specification and will have the following meanings unless otherwise indicated.

Formation: Hydrocarbon exploration processes, hydrocarbon recovery (also referred to as hydrocarbon production) processes, or any combination thereof may be performed on a formation. The formation refers to practically any volume under a surface. For example, the formation may be practically any volume under a terrestrial surface (e.g., a land surface), practically any volume under a seafloor, etc. A water column may be above the formation, such as in marine hydrocarbon exploration, in marine hydrocarbon recovery, etc. The formation may be onshore. The formation may be offshore (e.g., with shallow water or deep water above the formation). The formation may include faults, fractures, overburdens, underburdens, salts, salt welds, rocks, sands, sediments, pore space, etc. Indeed, the formation may include practically any geologic point(s) or volume(s) of interest (such as a survey area) in some embodiments.

The formation may include hydrocarbons, such as liquid hydrocarbons (also known as oil or petroleum), gas hydrocarbons (e.g., natural gas), solid hydrocarbons (e.g., asphaltenes or waxes), a combination of hydrocarbons (e.g., a combination of liquid hydrocarbons, gas hydrocarbons, and solid hydrocarbons), etc. Light crude oil, medium oil, heavy crude oil, and extra heavy oil, as defined by the American Petroleum Institute (API) gravity, are examples of hydrocarbons. Examples of hydrocarbons are many, and hydrocarbons may include oil, natural gas, kerogen, bitumen, clathrates (also referred to as hydrates), etc. The hydrocarbons may be discovered by hydrocarbon exploration processes.

The formation may also include at least one wellbore. For example, at least one wellbore may be drilled into the formation in order to confirm the presence of the hydrocarbons. As another example, at least one wellbore may be drilled into the formation in order to recover (also referred to as produce) the hydrocarbons. The hydrocarbons may be recovered from the entire formation or from a portion of the formation. For example, the formation may be divided into one or more hydrocarbon zones, and hydrocarbons may be recovered from each desired hydrocarbon zone. One or more of the hydrocarbon zones may even be shut-in to increase hydrocarbon recovery from a hydrocarbon zone that is not shut-in.

The formation, the hydrocarbons, or any combination thereof may also include non-hydrocarbon items. For example, the non-hydrocarbon items may include connate water, brine, tracers, items used in enhanced oil recovery or other hydrocarbon recovery processes, items from other treatments (e.g., items used in conformance control), etc.

In short, each formation may have a variety of characteristics, such as petrophysical rock properties, reservoir fluid properties, reservoir conditions, hydrocarbon properties, or any combination thereof. For example, each formation (or even zone or portion of the formation) may be associated with one or more of: temperature, porosity, salinity, permeability, water composition, mineralogy, hydrocarbon type, hydrocarbon quantity, reservoir location, pressure, etc. Indeed, those of ordinary skill in the art will appreciate that the characteristics are many, including, but not limited to: shale gas, shale oil, tight gas, tight oil, tight carbonate, carbonate, vuggy carbonate, unconventional (e.g., a rock matrix with an average pore size less than 1 micrometer), diatomite, geothermal, mineral, metal, a formation having a permeability in the range of 0.01 microdarcy to 10 millidarcy, a formation having a permeability in the range of 10 millidarcy to 40,000 millidarcy, etc.

The terms "formation", "subsurface formation", "hydrocarbon-bearing formation", "reservoir", "subsurface reservoir", "subsurface region of interest", "subterranean reservoir", "subsurface volume of interest", and the like may be used synonymously. The terms "formation", "hydrocarbons", and the like are not limited to any description or configuration described herein.

Wellbore: A wellbore refers to a single hole, usually cylindrical, that is drilled into the formation for hydrocarbon exploration, hydrocarbon recovery, surveillance, or any combination thereof. The wellbore is usually surrounded by the formation and the wellbore may be configured to be in fluidic communication with the formation (e.g., via perforations). The wellbore may also be configured to be in fluidic communication with the surface, such as in fluidic communication with a surface facility that may include oil/gas/water separators, gas compressors, storage tanks, pumps, gauges, sensors, meters, pipelines, etc.

The wellbore may be used for injection (sometimes referred to as an injection wellbore) in some embodiments. The wellbore may be used for production (sometimes referred to as a production wellbore) in some embodiments. The wellbore may be used for a single function, such as only injection, in some embodiments. The wellbore may be used for a plurality of functions, such as production then injection, in some embodiments. The use of the wellbore may also be changed, for example, a particular wellbore may be turned into an injection wellbore after a different previous use as a production wellbore. The wellbore may be drilled amongst existing wellbores, for example, as an infill wellbore. A wellbore may be utilized for injection and a different wellbore may be used for hydrocarbon production, such as in the scenario that hydrocarbons are swept from at least one injection wellbore towards at least one production wellbore and up the at least one production wellbore towards the surface for processing. On the other hand, a single wellbore may be utilized for injection and hydrocarbon production, such as a single wellbore used for hydraulic fracturing and hydrocarbon production. A plurality of wellbores (e.g., tens to hundreds of wellbores) are often used in a field to recover hydrocarbons.

The wellbore may have straight, directional, or a combination of trajectories. For example, the wellbore may be a vertical wellbore, a horizontal wellbore, a multilateral wellbore, an inclined wellbore, a slanted wellbore, etc. The wellbore may include a change in deviation. As an example, the deviation is changing when the wellbore is curving. In a horizontal wellbore, the deviation is changing at the curved section (sometimes referred to as the heel). As used herein, a horizontal section of a wellbore is drilled in a horizontal direction (or substantially horizontal direction). For example, a horizontal section of a wellbore is drilled towards the bedding plane direction. A horizontal section of a wellbore may be, but is not limited to, a horizontal section of a horizontal wellbore. On the other hand, a vertical wellbore is drilled in a vertical direction (or substantially vertical direction). For example, a vertical wellbore is drilled perpendicular (or substantially perpendicular) to the bedding plane direction.

The wellbore may include a plurality of components, such as, but not limited to, a casing, a liner, a tubing string, a heating element, a sensor, a packer, a screen, a gravel pack, artificial lift equipment (e.g., an electric submersible pump (ESP)), etc. The "casing" refers to a steel pipe cemented in place during the wellbore construction process to stabilize the wellbore. The "liner" refers to any string of casing in which the top does not extend to the surface but instead is suspended from inside the previous casing. The "tubing string" or simply "tubing" is made up of a plurality of tubulars (e.g., tubing, tubing joints, pup joints, etc.) connected together. The tubing string is lowered into the casing or the liner for injecting a fluid into the formation, producing a fluid from the formation, or any combination thereof. The casing may be cemented in place, with the cement positioned in the annulus between the formation and the outside of the casing. The wellbore may also include any completion hardware that is not discussed separately. If the wellbore is drilled offshore, the wellbore may include some of the previous components plus other offshore components, such as a riser.

The wellbore may also include equipment to control fluid flow into the wellbore, control fluid flow out of the wellbore, or any combination thereof. For example, each wellbore may include a wellhead, a BOP, chokes, valves, or other control devices. These control devices may be located on the surface, under the surface (e.g., downhole in the wellbore), or any combination thereof. In some embodiments, the same control devices may be used to control fluid flow into and out of the wellbore. In some embodiments, different control devices may be used to control fluid flow into and out of the wellbore. In some embodiments, the rate of flow of fluids through the wellbore may depend on the fluid handling capacities of the surface facility that is in fluidic communication with the wellbore. The control devices may also be utilized to control the pressure profile of the wellbore.

The equipment to be used in controlling fluid flow into and out of the wellbore may be dependent on the wellbore, the formation, the surface facility, etc. However, for simplicity, the term "control apparatus" is meant to represent any wellhead(s), BOP(s), choke(s), valve(s), fluid(s), and other equipment and techniques related to controlling fluid flow into and out of the wellbore.

The wellbore may be drilled into the formation using practically any drilling technique and equipment known in the art, such as geosteering, directional drilling, etc. Drilling the wellbore may include using a tool, such as a drilling tool that includes a drill bit and a drill string. Drilling fluid, such as drilling mud, may be used while drilling in order to cool the drill tool and remove cuttings. Other tools may also be used while drilling or after drilling, such as measurement-while-drilling (MWD) tools, seismic-while-drilling (SWD) tools, wireline tools, logging-while-drilling (LWD) tools, or other downhole tools. After drilling to a predetermined depth, the drill string and the drill bit are removed, and then the casing, the tubing, etc. may be installed according to the design of the wellbore.

The equipment to be used in drilling the wellbore may be dependent on the design of the wellbore, the formation, the hydrocarbons, etc. However, for simplicity, the term "drilling apparatus" is meant to represent any drill bit(s), drill string(s), drilling fluid(s), and other equipment and techniques related to drilling the wellbore.

The term "wellbore" may be used synonymously with the terms "borehole," "well," or "well bore." The term "wellbore" is not limited to any description or configuration described herein.

Hydrocarbon recovery: The hydrocarbons may be recovered (sometimes referred to as produced) from the formation using primary recovery (e.g., by relying on pressure to recover the hydrocarbons), secondary recovery (e.g., by using water injection (also referred to as waterflooding) or natural gas injection to recover hydrocarbons), enhanced oil recovery (EOR), or any combination thereof. Enhanced oil recovery or simply EOR refers to techniques for increasing the amount of hydrocarbons that may be extracted from the formation. Enhanced oil recovery may also be referred to as tertiary oil recovery. Secondary recovery is sometimes just referred to as improved oil recovery or enhanced oil recovery. EOR processes include, but are not limited to, for example: (a) miscible gas injection (which includes, for example, carbon dioxide flooding), (b) chemical injection (sometimes referred to as chemical enhanced oil recovery (CEOR) that includes, for example, polymer flooding, alkaline flooding, surfactant flooding, conformance control, as well as combinations thereof such as alkaline-polymer (AP) flooding, surfactant-polymer (SP) flooding, or alkaline-surfactant-polymer (ASP) flooding), (c) microbial injection, (d) thermal recovery (which includes, for example, cyclic steam and steam flooding), or any combination thereof. The hydrocarbons may be recovered from the formation using a fracturing process. For example, a fracturing process may include fracturing using electrodes, fracturing using fluid (oftentimes referred to as hydraulic fracturing), etc. The hydrocarbons may be recovered from the formation using radio frequency (RF) heating. Other hydrocarbon recovery processes may also be utilized to recover the hydrocarbons. Furthermore, those of ordinary skill in the art will appreciate that one hydrocarbon recovery process may also be used in combination with at least one other recovery process or subsequent to at least one other recovery process. Moreover, hydrocarbon recovery processes may also include other options.

Other definitions: The term "proximate" is defined as "near". If item A is proximate to item B, then item A is near item B. For example, in some embodiments, item A may be in contact with item B. For example, in some embodiments, there may be at least one barrier between item A and item B such that item A and item B are near each other, but not in contact with each other. The barrier may be a fluid barrier, a non-fluid barrier (e.g., a structural barrier), or any combination thereof. Both scenarios are contemplated within the meaning of the term "proximate."

The terms "comprise" (as well as forms, derivatives, or variations thereof, such as "comprising" and "comprises") and "include" (as well as forms, derivatives, or variations thereof, such as "including" and "includes") are inclusive (i.e., open-ended) and do not exclude additional elements or steps. For example, the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of 10 percent of the given numeric value provided such a deviation does not alter the end function or result of the value. Therefore, a value of about 1% can be construed to be a range from 0.9% to 1.1%. Furthermore, a range may be construed to include the start and the end of the range. For example, a range of 10% to 20% (i.e., range of 10%-20%) includes 10% and also includes 20%, and includes percentages in between 10% and 20%, unless explicitly stated otherwise herein. Similarly, a range of between 10% and 20% (i.e., range between 10%-20%) includes 10% and also includes 20%, and includes percentages in between 10% and 20%, unless explicitly stated otherwise herein.

The term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

It is understood that when combinations, subsets, groups, etc. of elements are disclosed (e.g., combinations of components in a composition, or combinations of steps in a method), that while specific reference of each of the various individual and collective combinations and permutations of these elements may not be explicitly disclosed, each is specifically contemplated and described herein. By way of example, if an item is described herein as including a component of type A, a component of type B, a component of type C, or any combination thereof, it is understood that this phrase describes all of the various individual and collective combinations and permutations of these components. For example, in some embodiments, the item described by this phrase could include only a component of type A. In some embodiments, the item described by this phrase could include only a component of type B. In some embodiments, the item described by this phrase could include only a component of type C. In some embodiments, the item described by this phrase could include a component of type A and a component of type B. In some embodiments, the item described by this phrase could include a component of type A and a component of type C. In some embodiments, the item described by this phrase could include a component of type B and a component of type C. In some embodiments, the item described by this phrase could include a component of type A, a component of type B, and a component of type C. In some embodiments, the item described by this phrase could include two or more components of type A (e.g., A1 and A2). In some embodiments, the item described by this phrase could include two or more components of type B (e.g., B1 and B2). In some embodiments, the item described by this phrase could include two or more components of type C (e.g., C1 and C2). In some embodiments, the item described by this phrase could include two or more of a first component (e.g., two or more components of type A (A1 and A2)), optionally one or more of a second component (e.g., optionally one or more components of type B), and optionally one or more of a third component (e.g., optionally one or more components of type C). In some embodiments, the item described by this phrase could include two or more of a first component (e.g., two or more components of type B (B1 and B2)), optionally one or more of a second component (e.g., optionally one or more components of type A), and optionally one or more of a third component (e.g., optionally one or more components of type C). In some embodiments, the item described by this phrase could include two or more of a first component (e.g., two or more components of type C (C1 and C2)), optionally one or more of a second component (e.g., optionally one or more components of type A), and optionally one or more of a third component (e.g., optionally one or more components of type B).

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have elements that do not differ from the literal language of the claims, or if they include equivalent elements with insubstantial differences from the literal language of the claims.

Unless defined otherwise, all technical and scientific terms used herein have the same meanings as commonly understood by one of skill in the art to which the disclosed invention belongs. All citations referred herein are expressly incorporated by reference.

Cation exchange capacity is loosely related to the surface charge of a material and it is the measure of the ability to reversibly adsorb cations. Exchangeable cations have varying hydration enthalpies due to the differences in their cation size and valence and as a result, the amount of water that can be adsorbed by a clay mineral is dependent on the total specific surface area, and the exchangeable cation type located in the interlayer regions and particle surfaces. While most clay minerals have some CEC e.g. (kaolinite, chlorite <5 meq/100 g [2], illite≈10-15 meq/100 g), smectite often has significantly greater CEC, sometimes an order of magnitude higher [3]. Thus, by measuring the CEC of a rock, one can estimate the approximate amount of smectite in the rock.

Several methods exist to measure the CEC of a rock, and most methods involve the complete exchange of cations present in the natural sample by a cationic species, such as $NH4$, $K+$, $Na2+$, methylene blue, Co(III)-hexamine3+, and Cu(II) ethylendiamine complex. Exchange is quantified by measuring the effluent solution by spectrophotometric techniques or by measuring the change in cation concentration in the fluid through mass spectroscopy. These methods, with some limitations, are effective CEC measurement methods, however, they are typically time intensive, require the use of chemicals which involve proper disposal, and a laboratory to store chemicals and house analytical equipment.

Relative permittivity (the real part of the complex permittivity) measures the degree to which a medium resists the flow of electric charge. Water is a polar molecule with a permanent dipole moment and will rotate to align with an applied electric field. This is taken advantage of in the frequency region where the dielectric response of the rock is governed by dipole polarization (~108 Hz). In this region, the effects of water, either in the form of adsorbed water on mineral surfaces, capillary water, or free water, makes permittivity measurements sensitive to CEC, and thus to the amount of smectite present in the rock.

As CEC is an important mineral property to characterize in the oil and gas industry, several avenues of proxy CEC analysis have been developed, including the use of magnetic susceptibility and dielectric permittivity. Specific to the use of dielectric analysis as a CEC tool, one first conventional methodology provides a set of equations derived from dimensional analysis to calculate CEC, however, these equations require surface area and porosity information to solve for CEC and these data are often not readily available. A second conventional methodology provides a standard test procedure for ultimately calculating the amount of hydratable clays in shales. This second conventional methodology involves several steps including saturating the sample in a K+ solution, centrifuging twice, washing the sample with rubbing alcohol, and taking the dielectric measurement. In this second conventional methodology, CEC is then calculated by a correlation between the dielectric constant and standard mixtures. A portable kit that includes all the equipment necessary to make the measurements is available for this second conventional methodology. A. A. Garrouch, "Predicting the cation exchange capacity of reservoir rocks from complex dielectric permittivity measurements," *Geophysics*, vol. 83, no. 1, pp. MR1-MR14, January-February 2018, doi: 10.1190/GE02017-0035.1 is incorporated by reference. P. K. Leung, R. P. Steiger, "Dielectric constant measurements: a new, rapid method to characterize shale at the wellsite," presented at SPE/IADC Drilling Conference, New Orleans, La., USA, February 18-21, Paper: SPE-23887-MS is incorporated by reference. While both the first and second conventional methodologies offer ways to calculate CEC from dielectric measurements, extra labor is still required to either attain additional data to calculate CEC (i.e., the first conventional methodology) or to prepare the sample for dielectric analysis (i.e., the second conventional methodology).

Provided herein are various embodiments of determining a cation exchange capacity of a rock sample. One embodiment of a method of analyzing a rock sample comprises equilibrating the rock sample to a relative humidity, performing a dielectric permittivity measurement on the rock sample at the relative humidity, and determining a cation exchange capacity of the rock sample based on the dielectric permittivity measurement. One embodiment of a method of determining a cation exchange capacity of a rock sample comprises receiving a dielectric permittivity measurement on the rock sample, and determining a cation exchange capacity for the rock sample based on the dielectric permittivity measurement of the rock sample and a relationship between cation exchange capacity and dielectric permittivity measurements for mineral mixtures corresponding to a range of cation exchange capacity values.

As will be discussed further herein, one or more equations may be previously generated using mineral mixtures (e.g., quartz and smectite mixtures), and then the one or more equations may be utilized to determine the cation exchange capacity of a new rock sample. For example, the one or more equations may be previously generated in association with a frequency and a temperature, and then the one or more equations may be utilized to determine the cation exchange capacity of the new rock sample at the frequency and the temperature. If the temperature and/or the frequency associated with the new rock sample are different than the temperature and/or the frequency associated with the one or more equations, then the one or more equations may be regenerated for the new frequency and/or the new temperature. The one or more equations that were regenerated at the new frequency and/or the new temperature may then be utilized to determine the cation exchange capacity for the new rock sample at the new frequency and/or the new temperature. The new rock sample undergoes less preparation to determine the cation exchange capacity as compared to conventional methodologies.

Advantageously, a person of ordinary skill in the art may appreciate that embodiments consistent with the present disclosure may provide a simpler, non-chemical based approach of determining the cation exchange capacity of the rock sample. For example, some embodiments may determine a simplified cation exchange capacity proxy using direct dielectric permittivity measurements. Furthermore, the cation exchange capacity of the rock sample may be determined in a non-laboratory setting (e.g., as a wellsite), in a laboratory setting, or both. Indeed, some embodiments may determine cation exchange capacity quickly and without the use of chemicals or complicated analytical equipment so that cation exchange capacity data can be available quickly to aid in decision making while drilling. Determining the cation exchange capacity of clay bearing rocks is a useful tool to estimate smectite content, or amount of swelling clay in the rock, and is referenced across many aspects of oil and gas exploration.

Indeed, a person of ordinary skill in the art may appreciate that embodiments consistent with the present disclosure may provide a portable cation exchange capacity analysis technique that does not require significant sample preparation or the use of chemicals. Additionally, some embodiments consistent with the present disclosure may be used to quickly determine cation data so that drilling engineers and geologists may assess changes in the swelling potential of rocks being drilled and account for potentially impacted processes in real-time. Moreover, some embodiments consistent with the present disclosure provide a procedure and a set of equations to determine the cation exchange capacity that can be developed for specific laboratory/field conditions where relative humidity (and temperature) conditions are often not constant. For example, after the equations are established (see EQUATION GENERATION section herein), the embodiment illustrated in FIG. 1A or FIG. 12 may be followed to determine the cation capacity exchange for a rock sample.

Turning to FIG. 1A, this figure illustrates one embodiment of a method 100 of determining a cation exchange capacity of a rock sample. At 105, the method 100 includes equilibrating the rock sample to a relative humidity. In one embodiment, the rock sample may comprise fluid, such as, but not limited to, water, hydrocarbons (e.g., liquid hydrocarbons), a combination of water and hydrocarbons (e.g., liquid hydrocarbons), etc. In one embodiment, the rock sample comprises drill cutting, a core sample, a soil sample, an outcrop sample, a mudcake sample, or any combination thereof. For example, the core sample may comprise rock and fluid retrieved from a wellbore drilled into a reservoir using a pressure coring process, a rotary sidewall coring process, etc. The core sample may be a subsample of a longer core sample.

In one embodiment, the rock sample comprises rock particles. In one embodiment, the rock sample comprises rock particles sized at least 0.1 millimeters (e.g., at least 0.2 millimeters, at least 0.25 millimeters, at least 0.3 millimeters, at least 0.35 millimeters, at least 0.4 millimeters, at least 0.45 millimeters, at least 0.5 millimeters, at least 0.55 millimeters, at least 0.6 millimeters, at least 0.65 millimeters, at least 0.7 millimeters, or at least 0.75 millimeters). In some embodiments, the rock sample comprises rock particles sized 0.8 millimeters or less (e.g., 0.75 millimeters or less, 0.65 millimeters or less, 0.6 millimeters or less, 0.55 millimeters or less, 0.5 millimeters or less, 0.45 millimeters or less, 0.42 millimeters or less, 0.4 millimeters or less, 0.35 millimeters or less, 0.3 millimeters or less, 0.25 millimeters or less, 0.2 millimeters or less, or 0.15 millimeters or less). In some embodiments, the rock sample comprises rock particles sized less than about 0.8 millimeters. In some embodiments, the rock sample comprises rock particles sized less than about 0.45 millimeters. In some embodiments, the rock sample comprises rock particles sized less than about 0.42 millimeters. The rock sample comprises rock particles that may be sized in an amount ranging from any of the minimum values described above to any of the maximum values described above. For example, in some embodiments, the rock sample comprises rock particles sized between 0.1 millimeters and 0.8 millimeters (e.g., between 0.25 millimeters and 0.75 millimeters, between 0.25 millimeters and 0.5 millimeters, between 0.3 millimeters and 0.5 millimeters, between 0.1 millimeters and 0.41 millimeters, between 0.25 millimeters and 0.41 millimeters, or between 0.4 millimeters and 0.45 millimeters). As will be discussed further herein at 125, in some embodiments, the rock sample may be broken to get the rock particles. The term "rock sample" is not limited to any description or configuration described herein.

The rock sample (e.g., such as the rock particles) may be equilibrated in practically any manner known to those of ordinary skill in the art. For example, the rock sample may be equilibrated in a desiccator, such as a relative humidity controlled desiccator, on a tabletop, etc. In one embodiment, the rock sample is equilibrated to the relative humidity of at least 8% (e.g., at least 10%, at least 15%, at least 20%, at least 25%, at least 30%, at least 35%, at least 40%, at least 45%, at least 50%, at least 55%, at least 60%, at least 65%, or at least 70%). In some embodiments, the rock sample is equilibrated to the relative humidity of 75% or less (e.g., 72% or less, 70% or less, 65% or less, 60% or less, 55% or less, 50% or less, 45% or less, 40% or less, 35% or less, 30% or less, 25% or less, 20% or less, 15% or less, or 10% or less). The rock sample is equilibrated to the relative humidity in an amount ranging from any of the minimum values described above to any of the maximum values described above. For example, in some embodiments, the rock sample is equilibrated to the relative humidity of between 8% and 75% (e.g., between 8% and 72%, between 8% and 50%, between 8% and 25%, between 25% and 50%). In some embodiments, the rock sample is equilibrated to the relative humidity of between about 8% and about 75%, such as ±10 percent of 8% and/or 10 percent of 75%. In one embodiment, the relative humidity is the same relative humidity associated with the one or more equations at 115 of the method 100. However, the same relative humidity associated with the one or more equations at 115 of the method 100 does not need to be used in a different embodiment.

In some embodiments, the rock sample may be equilibrated to the relative humidity for at least one hour (e.g., at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, or at least 48 hours). In some embodiments, the rock sample may be equilibrated to the relative humidity for 48 hours or less (e.g., 47 hours or less, 46 hours or less, 45 hours or less, 44 hours or less, 43 hours or less, 42 hours or less, 41 hours or less, 40 hours or less, 39 hours or less, 38 hours or less, 37 hours or less, 36 hours or less, 35 hours or less, 34 hours or less, 33 hours or less, 32 hours or less, 31 hours or less, 30 hours or less, 29 hours or less, 28 hours or less, 27 hours or less, 26 hours or less, 25 hours or less, 24 hours or less, 23 hours or less, 22 hours or less, 21 hours or less, 20 hours or less, 19 hours or less, 18 hours or less, 17 hours or less, 16 hours or less, 15 hours or less, 14 hours or less, 13 hours or less, 12 hours or less, 11 hours or less, 10 hours or less, 9 hours or less, 8 hours or less, 7 hours or less, 6 hours or less, 5 hours or less, 3 hours or less, 2 hours or less, or 1 hour or less). The rock sample may be equilibrated to the relative humidity in an amount ranging from any of the minimum values described above to any of the maximum values described above. For example, in some embodiments, the rock sample may be equilibrated to the relative humidity for between 1 hour and 48 hours (e.g., between 1 hour and 24 hours, between 1 hour and 12 hours, between 1 hour and 6 hours, or between 1 hour and 3 hours).

At 110, the method 100 includes performing a dielectric permittivity measurement on the rock sample at the relative humidity. In one embodiment, the dielectric permittivity measurement on the rock sample (e.g., on the rock particles) is performed using a handheld dielectric probe. For example, the Dielectric Assessment Kit System (Schmid & Partner Engineering AG, Switzerland) with a Planar R140 Vector Reflectometer (Copper Mountain Technologies vector network analyzer) and a DAK-3.5 probe may be used to perform the dielectric permittivity measurements. The Vector Network Analyzer (VNA) operates from 85 MHz to 1.4 GHz, and the Depth of Investigation (DOI) of the DAK-3.5 probe is ~3 mm. The circular probe end is ~1 inch in diameter. However, a different dielectric probe may be utilized.

In one embodiment, the dielectric permittivity measurement on the rock sample is performed at a frequency of at least 80 megahertz (e.g., at least 100 megahertz, at least 150 megahertz, at least 200 megahertz, at least 250 megahertz, at least 300 megahertz, at least 350 megahertz, at least 400 megahertz, at least 450 megahertz, at least 500 megahertz, or at least 550 megahertz). In some embodiments, the dielectric permittivity measurement on the rock sample is performed at a frequency of 600 megahertz or less (e.g., 550 megahertz or less, 500 megahertz or less, 450 megahertz or less, 400 megahertz or less, 350 megahertz or less, 300 megahertz or less, 250 megahertz or less, 200 megahertz or less, 150 megahertz or less, or 100 megahertz or less). In one embodiment, the dielectric permittivity measurement on the rock sample is performed at about 120 megahertz, such as ±10 percent of 120 megahertz. The dielectric permittivity measurement on the rock sample is performed at a frequency in an amount ranging from any of the minimum values described above to any of the maximum values described above. For example, in some embodiments, the dielectric permittivity measurement on the rock sample is performed at a frequency between 80 megahertz and 600 megahertz (e.g., between 80 megahertz and 300 megahertz, 80 megahertz and 150 megahertz, 100 megahertz and 300 megahertz, or 100 megahertz and 450 megahertz. In one embodiment, the dielectric permittivity measurement on the rock sample is performed at a frequency between about 80 megahertz and about 600 megahertz, such as ±10 percent of 80 megahertz and/or ±10 percent of 600 megahertz. In one embodiment, the frequency is the same frequency associated with the one or more equations at 115 of the method 100.

In one embodiment, the temperature is the same temperature associated with the one or more equations at 115 of the method 100. In one embodiment, the rock sample is maintained at a constant temperature while performing the dielectric permittivity measurement.

At 115, the method 100 includes determining a cation exchange capacity of the rock sample based on the dielectric permittivity measurement. In one embodiment, the cation exchange capacity for the rock sample (e.g., for the rock particles) is determined using the following equation:

$$CEC = S_{RH} \varepsilon'_r + c_{RH} \quad \text{Equation A}$$

where $\varepsilon'_r$ represents the dielectric permittivity measurement on the rock sample, $S_{RH}$ represents a slope for a linear relationship between the cation exchange capacity and the dielectric permittivity measurement as a function of relative humidity, and $c_{RH}$ represents a y-intercept constant for the linear relationship between the cation exchange capacity and the dielectric permittivity measurement as the function of relative humidity. CEC stands for the cation exchange capacity. The Equation A was previously generated, and the Equation A may be utilized at 115.

In one embodiment, $S_{RH}$ is segmented into a plurality of regions that each span a range of relative humidities, the regions being segmented by changes in a slope of a linear relationship between $S_{RH}$ and relative humidity. In one embodiment, $S_{RH}$ and $c_{RH}$ are determined based on a plot of cation exchange capacities and dielectric permittivity measurements as a function of relative humidity for mineral mixtures corresponding to a range of cation exchange capacity values. For example, the dielectric permittivity measurement for the rock sample is performed (at 110 of the method 100) at a temperature and/or a frequency that is consistent with the dielectric permittivity measurements of the mineral mixtures.

For example, $S_{RH}$ and $c_{RH}$ may be determined based on a plot of cation exchange capacities and dielectric permittivity measurements as a function of relative humidity for known quartz-smectite ratios. In one embodiment, a desiccant is used to obtain a plurality of relative humidities for the known quartz-smectite ratios. In one embodiment, the desiccant is selected from lithium chloride (LiCl), lithium iodide (LiI), magnesium chloride (MgCl), potassium carbonate (K2CO3), sodium bromide (NaBr), sodium chloride (NaCl), or any combination thereof. A single desiccant or a plurality of desiccants may be utilized depending on the plurality of relative humidities to be obtained.

Optionally, at 115, a correction factor is applied to the cation exchange capacity calculated for the rock sample. In one embodiment, the cation exchange capacity for the rock sample (e.g., for the rock particles) is determined using the following equation:

$$CEC = S_{RH} \varepsilon'_r + c_{RH} + C \quad \text{Equation B}$$

where $\varepsilon'_r$ represents the dielectric permittivity measurement on the rock sample, $S_{RH}$ represents a slope for a linear relationship between the cation exchange capacity and the dielectric permittivity measurement as a function of relative humidity, $c_{RH}$ represents a y-intercept constant for the linear relationship between the cation exchange capacity and the dielectric permittivity measurement as the function of relative humidity, and C represents a correction factor applied to the cation exchange capacity. CEC stands for the cation exchange capacity. The Equation B was previously generated, and the Equation B may be utilized at 115.

Similarly, in one embodiment, $S_{RH}$ is segmented into a plurality of regions that each span a range of relative humidities, the regions being segmented by changes in a slope of a linear relationship between $S_{RH}$ and relative humidity. In one embodiment, $S_{RH}$ and $c_{RH}$ are determined based on a plot of cation exchange capacities and dielectric permittivity measurements as a function of relative humidity for mineral mixtures corresponding to a range of cation exchange capacity values. For example, the dielectric permittivity measurement for the rock sample is performed (at 110 of the method 100) at a temperature and/or a frequency that is consistent with the dielectric permittivity measurements of the mineral mixtures.

For example, $S_{RH}$, $c_{RH}$, and C may be determined based on a plot of cation exchange capacities and dielectric permittivity measurements as a function of relative humidity for known quartz-smectite ratios. In one embodiment, a desiccant is used to obtain a plurality of relative humidities for the known quartz-smectite ratios. In one embodiment, the desiccant is selected from lithium chloride (LiCl), lithium iodide (LiI), magnesium chloride (MgCl), potassium carbonate (K2CO3), sodium bromide (NaBr), sodium chloride (NaCl), or any combination thereof. A single desiccant or a plurality of desiccants may be utilized depending on the plurality of relative humidities to be obtained.

In one embodiment, the dielectric permittivity measurement for the rock sample is performed at a temperature that is consistent with the dielectric permittivity measurements of the mineral mixture. Regarding the term "consistent", it may depend on the embodiment. Regarding "consistent," in one embodiment, the temperature used with the dielectric permittivity measurement for the rock sample is the same temperature used with the dielectric permittivity measurements of the mineral mixture, for example, both temperatures are 21 Degrees Celsius. The same temperature may lead to more accurate cation exchange capacities.

However, regarding "consistent," in one embodiment, the temperature used with the dielectric permittivity measurement for the rock sample is ±10 percent of the temperature used with the dielectric permittivity measurements of the mineral mixture. Regarding "consistent," in one embodiment, the temperature range used with the dielectric permittivity measurement for the rock sample is the same temperature range used with the dielectric permittivity measurements of the mineral mixture. These similar temperatures may lead to less accurate cation exchange capacities that may still be utilized in some contexts.

In one embodiment, the dielectric permittivity measurement for the rock sample is performed at a frequency that is consistent with the dielectric permittivity measurements of the mineral mixture. Regarding the term "consistent", it may depend on the embodiment. Regarding "consistent," in one embodiment, the frequency used with the dielectric permittivity measurement for the rock sample is the same frequency used with the dielectric permittivity measurements of the mineral mixture, for example, both frequencies are 120 MHz. The same frequency may lead to more accurate cation exchange capacities.

However, regarding "consistent," in one embodiment, the frequency used with the dielectric permittivity measurement for the rock sample is ±10 percent of the frequency used with the dielectric permittivity measurements of the mineral mixture. Regarding "consistent," in one embodiment, the frequency range used with the dielectric permittivity measurement for the rock sample is the same frequency range used with the dielectric permittivity measurements of the mineral mixture. These similar frequencies may lead to less accurate cation exchange capacities that may still be utilized in some contexts.

In one embodiment, the dielectric permittivity measurement for the rock sample is performed at a relative humidity that is consistent with the dielectric permittivity measurements of the mineral mixture. Regarding the term "consistent", it may depend on the embodiment. Regarding "consistent," in one embodiment, the relative humidity used with the dielectric permittivity measurement for the rock sample is the same relative humidity used with the dielectric permittivity measurements of the mineral mixture. The same relative humidity may lead to more accurate cation exchange capacities.

However, regarding "consistent," in one embodiment, the relative humidity used with the dielectric permittivity measurement for the rock sample is ±10 percent of the relative humidity used with the dielectric permittivity measurements of the mineral mixture. Regarding "consistent," in one embodiment, the relative humidity range used with the dielectric permittivity measurement for the rock sample is the same relative humidity range used with the dielectric permittivity measurements of the mineral mixture, such as relative humidity range 8%-75%. These similar relative humidities may not adversely impact the accuracy of the cation exchange capacities that are determined. Indeed, in some embodiments, the same frequencies and/or the same temperatures (and not the same relative humidities) may impact the accuracy of the cation exchange capacities that are determined.

EQUATION GENERATION: Generation of the Equation A and the Equation B are discussed in more detail in the following paper: (a) Stokes, et al., A new CEC measurement proxy using high-frequency dielectric analysis of crushed rock, SCA2019-032, 2019 and (b) Stokes et al., A new CEC measurement proxy using high-frequency dielectric analysis of crushed rock, PETROPHYSICS, VOL. 61, NO. 2 (APRIL 2020), pages 179-188, each of which is incorporated by reference. This equation generation section (i.e., subsections 2.1, 2.2, 3.1, 3.2, 3.3, and 4.1 herein) discusses the paper, the study in the paper, and the method/methodology in the paper. Thus, generation of the Equation A and the Equation B are discussed in more detail in this equation generation section. Embodiments consistent with generating one or more equations at some point in time, and subsequently using the one or more equations to determine the cation exchange capacity of the rock sample (e.g., the rock particles) at 115, are illustrated in FIGS. 1B-10. Of note, the claims are not limited to any embodiments discussed in the paper or any embodiments discussed herein.

Figure 2B:
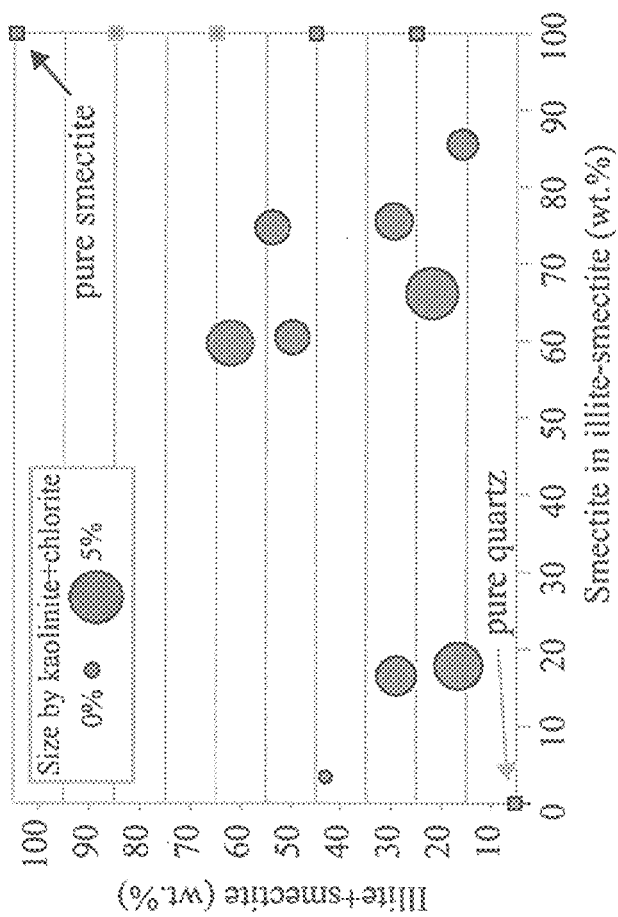
FIG. 2B illustrates illite-smectite wt. % vs. % smectite in illite-smectite calculated using Equation (1). Data points are sized by kaolinite+chlorite wt %.
Figure 2A:
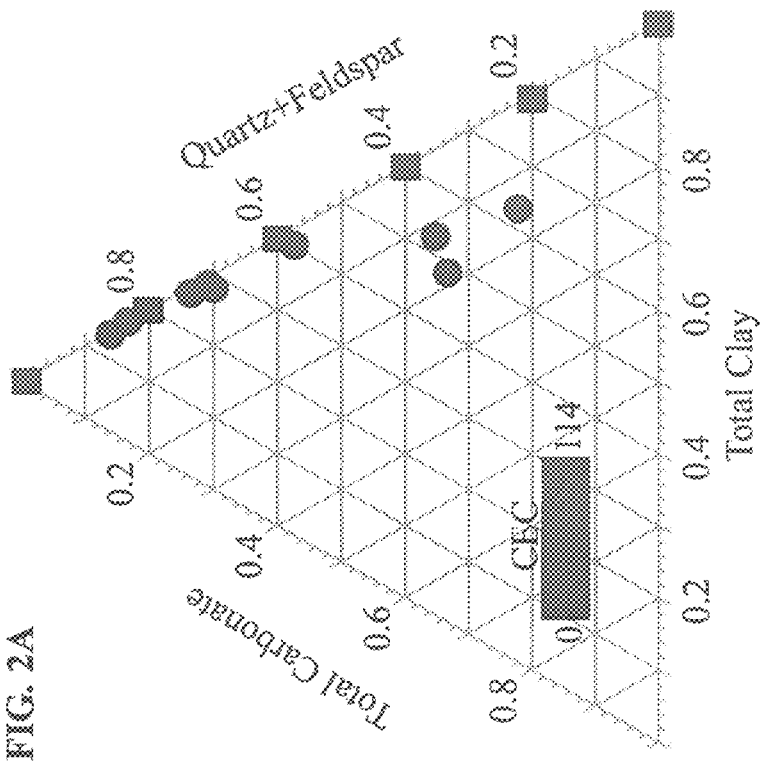
FIG. 2A illustrates a summary of sample mineralogy on a ternary diagram including both quartz:smectite mixtures (squares) and rock powders (circles). Samples are colored by their CEC values from laboratory measurements.

2.1 Sample selection and characterization: Two sets of samples were prepared for this study: 1) quartz-smectite mixtures and 2) rock powders from a variety of sedimentary rock types. Rock samples were selected based on their bulk mineralogy as determined by X-ray diffraction (XRD) analysis and bulk CEC values to obtain a decent range of rock types and CEC values up to 45 meq/100 g (FIG. 2A). Porosity data was collected on 7 of the 9 rock samples from co-located plugs by Hg porosimetry analysis on oven-dried and Dean Stark extracted material. Porosity values obtained using this method range between 7-23%. Detailed information about the clay compositions and amounts as determined by XRD analysis are shown in FIG. 2B. FIG. 2B shows illite-smectite wt. % plotted against the % smectite in illite-smectite (I-S) calculated using Equation (1). In this Equation (1), % S in I-S is determined by assigning the bulk rock CEC to the total illite-smectite ($CEC_{meas}$) wt. % and normalized on a difference between pure illite end member ($CEC_I$=15 meq/100 g) and pure smectite end member ($CEC_S$=100 meq/100 g).

$$\% \, S \, in \, I-S = \frac{CEC_{meas} - CEC_I}{CEC_S - CEC_I} \times 100 \quad \text{Equation (1)}$$

Data points in FIG. 2B are sized by kaolinite+chlorite which does not exceed 5 wt. %. Both kaolinite and chlorite have a low CEC (<10 meq/100 g) and are typically not considered significant contributors to bulk CEC.

The quartz-smectite standards were prepared by mechanically homogenizing 20% proportions by weight of pure quartz and a pure smectite (Tsukinuno montmorillonite JCSS-1301 distributed by The Clay Science Society of Japan) standard. Prior to homogenization, the quartz was comminuted in a McCrone mill for 5 minutes so that the quartz particle size approximately matched that of the smectite standard. The rock powders were prepared by hand grinding the material in a mortar and pestle to pass through a 40 mesh (0.42 mm) sieve. This methodology for preparing the rock powders avoids common issues associated with artificially altering the CEC via sample preparation. Hand grinding minimizes shearing which might delaminate clay particles, and the particle size associated with a 40 mesh sieve is, for most rocks, larger than the average phyllosilicate grain size thus not increasing the surface area of the individual grains.

Both the quartz-smectite mixtures and rock powders were dried in an oven at 105° C. for 48 hours to ensure that the majority of clay bound $H_2O$ was removed. Approximately 3 grams of material were loaded into a shallow plastic holder prior to being placed in the first relative humidity (RH) controlled desiccator. Samples were equilibrated for ~48 hours at each RH prior to dielectric analysis at each stage.

Splits were taken from all samples for CEC analysis and from the crushed rock samples for XRD analysis. These data are summarized in FIG. 2A. CEC measurements were done using the Co(III)-hexamine3+ cation exchange, spectrophotometric technique outlined by C. Bardon, "Recommandations pour la détermination expérimentale de la capacité d'échange de cations des milieux argileux," Rev. Inst. Fr. Pet., vol. 38, no. 5, pp. 621-626, September-October 1983, doi: 10.2516/ogst:1983037, which is incorporated by reference. The rock powders were prepared for XRD analysis following the methods described in Środoń et al. (2001) and Omotoso et al. (2006) to make randomly oriented powder mounts. The following references are incorporated by reference: J. Środoń, V. A. Drits, D. K. McCarty, J. C. C. Hsieh, D. D. Eberl, "Quantitative XRD analysis of clay-rich rocks from random preparations," Clay Clay Miner., vol. 49, no. 6, pp. 514-528, January 2001, doi: 10.1346/CCMN.2001.0490604 and O. Omotoso, D. K. McCarty, S. Hillier, R. Kleeberg, "Some successful approaches to quantitative mineral analysis as revealed by the 3rd Reynolds Cup contest," Clay Clay Miner., vol. 54, no. 6, pp. 748-760, December 2006, doi: 10.1346/CCMN.2006.0540609. The phase quantification was accomplished using software, which is a modification of a technique published by F. H. Chung, "Quantitative interpretation of X-ray diffraction patterns of mixtures. I. Matrix-flushing method for quantitative multicomponent analysis," *J. Appl. Crystallogr.*, vol. 7, no. 6, pp. 519-525, December 1974, doi: 10.1107/S0021889874010375, which is incorporated by reference. The Chung reference was utilized to determine mineralogy from xray defraction data, however, this is not necessary to determine the CEC and some embodiments do not determine mineralogy.

Relative humidity was controlled by using a series of saturated salt solutions in desiccation chambers and monitored by a barometric pressure-temperature-relative humidity data logger located inside the chamber. In increasing order of RH, the salts used in this study included lithium chlorite (LiCl), lithium iodide (LiI), potassium acetate ($CH_3CO_2K$), magnesium chlorite (MgCl), potassium carbonate ($K_2CO_3$), sodium bromide (NaBr), and sodium chloride (NaCl). To achieve the RH between LiCl and LiI (RH=11.2%), equal amounts of two saturated salt solutions (LiCl and LiI) were placed in separate containers in a desiccator. An additional RH dataset was collected by leaving the samples to equilibrate in the room RH (58.8%) for 24 hours. Room RH was monitored during the equilibration and did not deviate more than ±1.5%.

Water vapor adsorption analysis using the Dynamic Vapor Adsorption (DVS) machine developed by Surface Measurement Systems Ltd. was used to quantify the amount of water adsorbed by smectite at the specific RH conditions investigated in this study. This specific machine uses a gravimetric sorption technique that measures how quickly and how much of a solvent is adsorbed by a sample.

Figure 3:
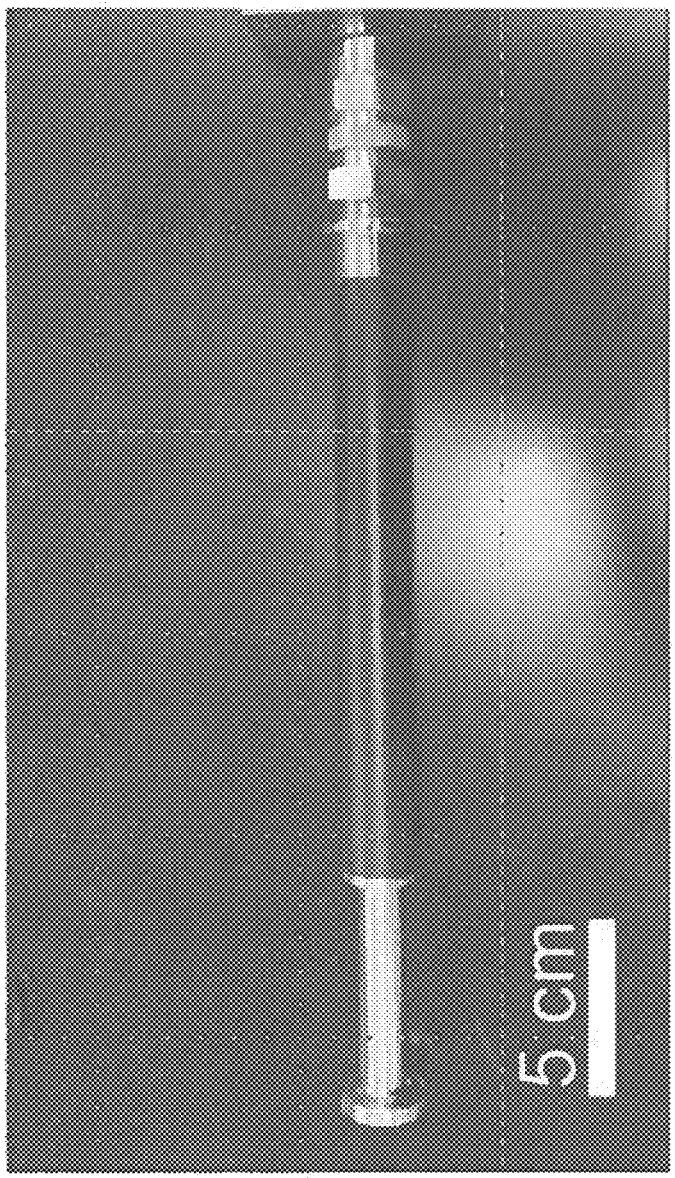
FIG. 3 illustrates one embodiment of a handheld probe for performing a dielectric permittivity measurement.

2.2 Dielectric measurement method: The Dielectric Assessment Kit System (Schmid & Partner Engineering AG, Switzerland) with a Planar R140 Vector Reflectometer (Copper Mountain Technologies vector network analyzer) and a DAK-3.5 probe was used to perform the laboratory dielectric measurements on each of the powder samples (FIG. 3). The Vector Network Analyzer (VNA) operates from 85 MHz to 1.4 GHz, and the Depth of Investigation (DOI) of the DAK-3.5 probe is ~3 mm.

Figure 4:
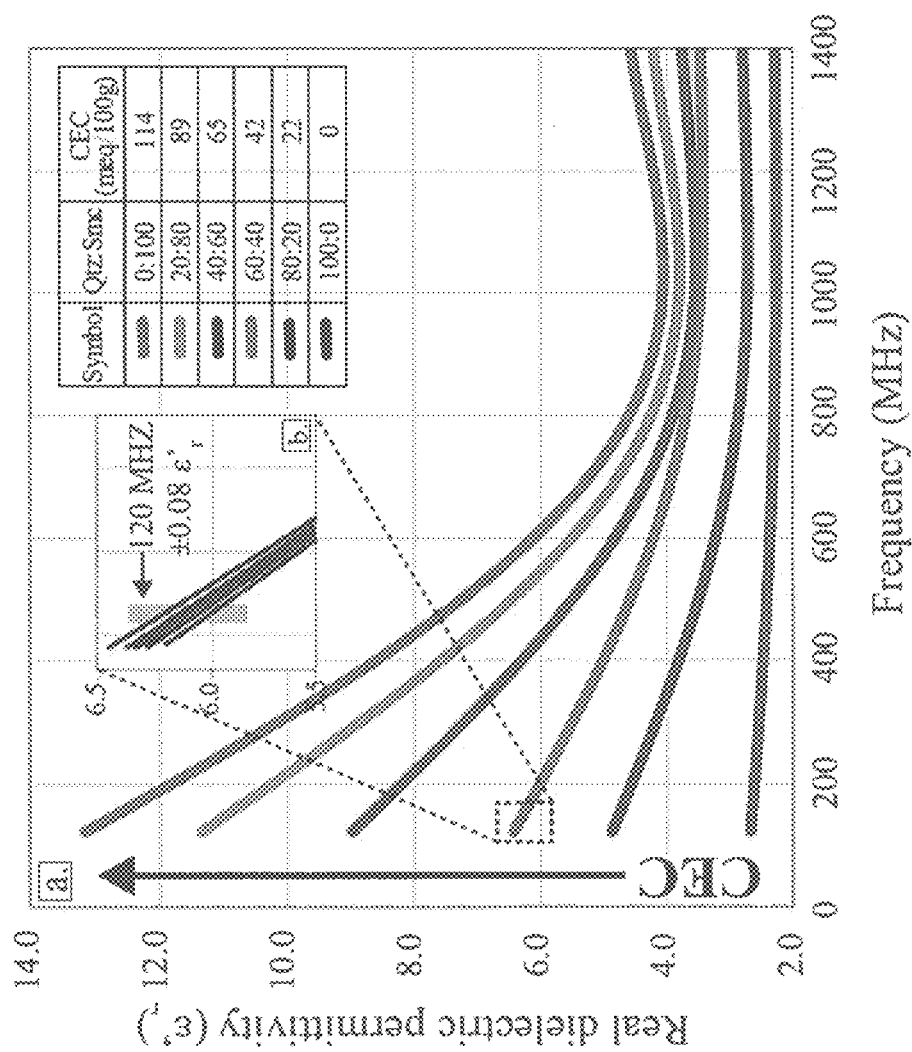
FIG. 4 illustrates real dielectric permittivity curves across the full frequency range for the 6 quartz-smectite used in the study.

The dielectric probe was always calibrated at room temperature (~21° C.) before usage. During the measurement at each designated RH, the probe remained vertical with the active surface area directly touching the top of the sample. A small amount of pressure was used to minimize the gap between the probe and the sample. After the permittivity readings stabilized, the values within the entire sweeping range (5 MHz resolution) were recorded (FIG. 4). The same measurement was repeated five times on each sample to ensure the reliability of the measurement and the average of those readings was used in the study. The typical observed $\varepsilon'_r$ range from 5 repeat measurements at 120 MHz is +0.08 (FIG. 4). FIG. 4 shows the influence of CEC on the dielectric response across the full range of frequencies. The largest difference between these curves is at the lower frequencies, thus, the real dielectric permittivity at 120 MHz was read for this study.

It should be noted that the laboratory RH was typically ~55%, consequently collecting the data for the lower RH conditions had to be done quickly. If a sample was exposed to the room RH conditions for more than 1 minute, it was placed back in the desiccator to re-equilibrate to the low RH condition and then analyzed again. As a result, the datasets for the RH conditions <30% took many days to collect.

Figure 5:
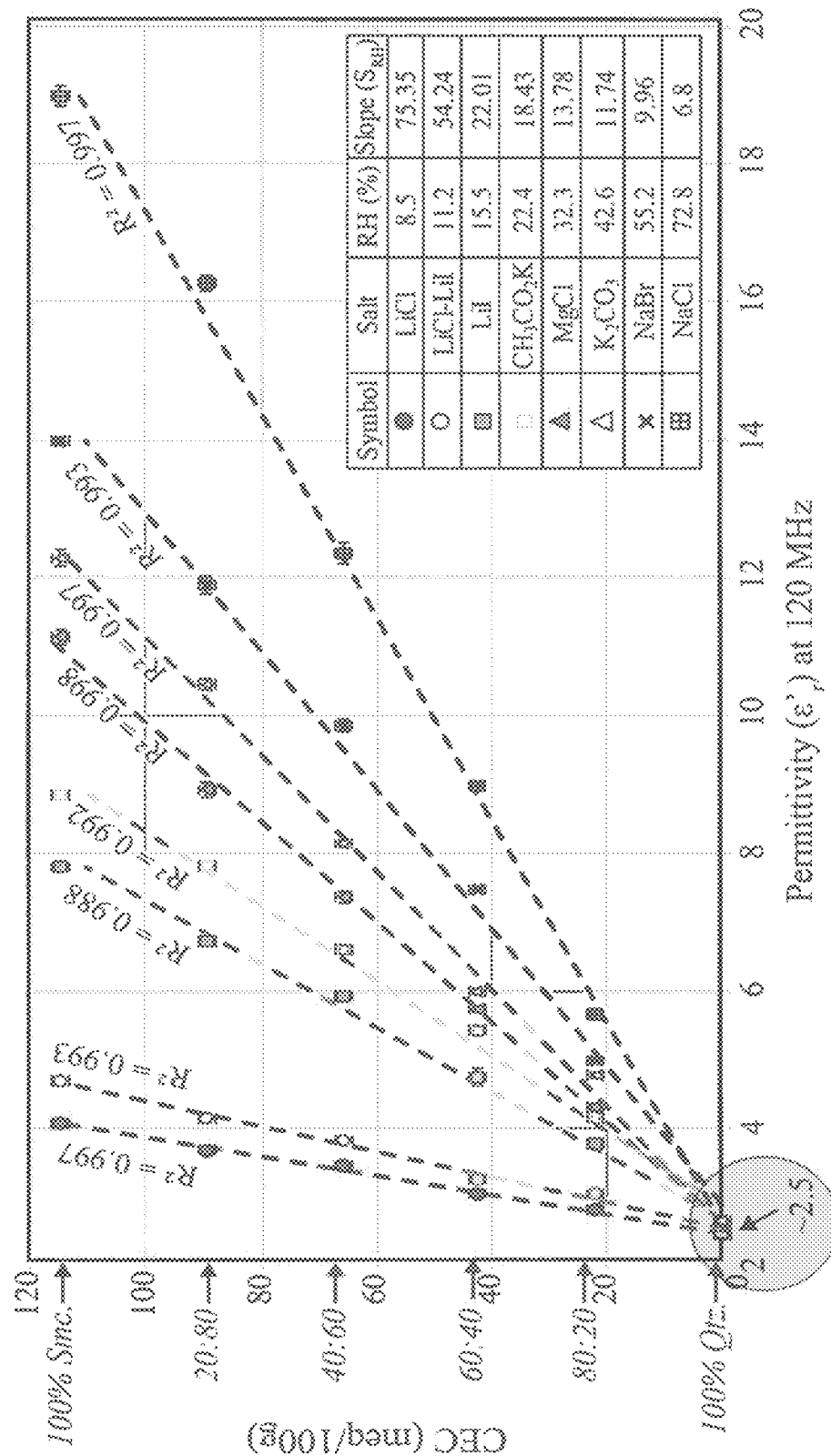
FIG. 5 illustrates electric permittivity at 120 MHz results from the 6 quartz-smectite mixtures at 8 different RH conditions. All data was collected at 21° C. Dashed lines and corresponding R2 values are the best fit line for each dataset. CEC error from laboratory measurements is ±1.8 meq/100 g and permittivity errors are from the range of values for the 5 repeat dielectric analyses collected on every sample at each RH. Quartz:smectite ratios are noted in grey italic lettering on the left side of the plot.

3.1 Dielectric Results—3.1.1 Quartz-smectite mixtures: Dielectric measurements of the quartz-smectite mixtures were collected to characterize and quantify the relationship between CEC, permittivity, and relative humidity. These results are shown in FIG. 5. Each RH dataset shows a very strong correlation between permittivity and CEC with $R^2$ values >0.98. The pure quartz sample (CEC=0) has a relatively constant permittivity value of ~2.5 despite the large range of RH conditions. At this point in the study, had the slope (and y-intercept) differences between each dataset showed a linear relationship with RH, a CEC calculation would be straightforward using a line equation and a multiplication factor for the slope-RH relationship. However, these datasets yield a non-linear relationship between the slope ($S_{RH}$), y-intercept constant ($c_{RH}$), and relative humidity which needs to be further constrained to successfully calculate CEC using Equation (2).

$$CEC = S_{RH}\varepsilon'_r + c_{RH} \qquad \text{Equation (2)}$$

Figure 6:
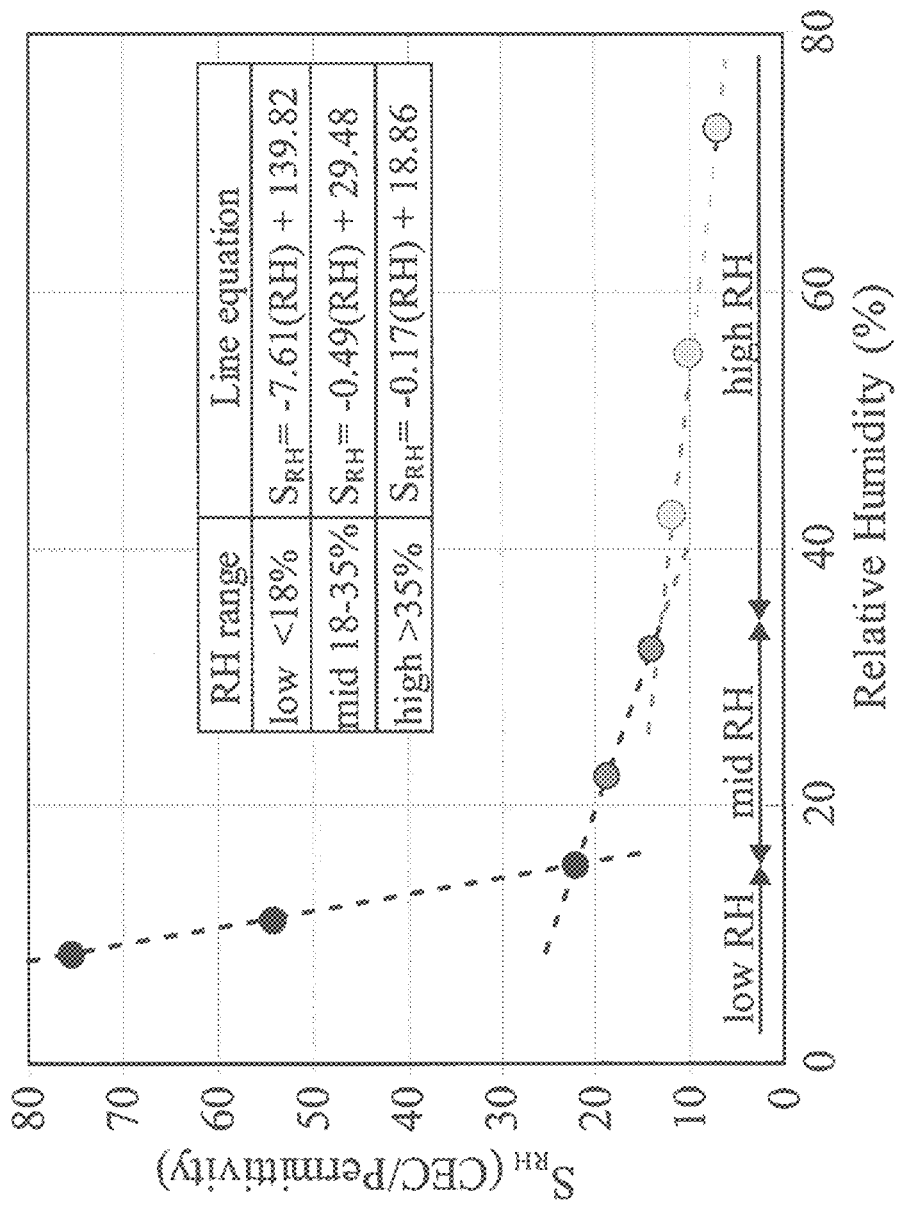
FIG. 6 illustrates a relationship between the slopes derived from FIG. 5 and relative humidity.
Figure 7:
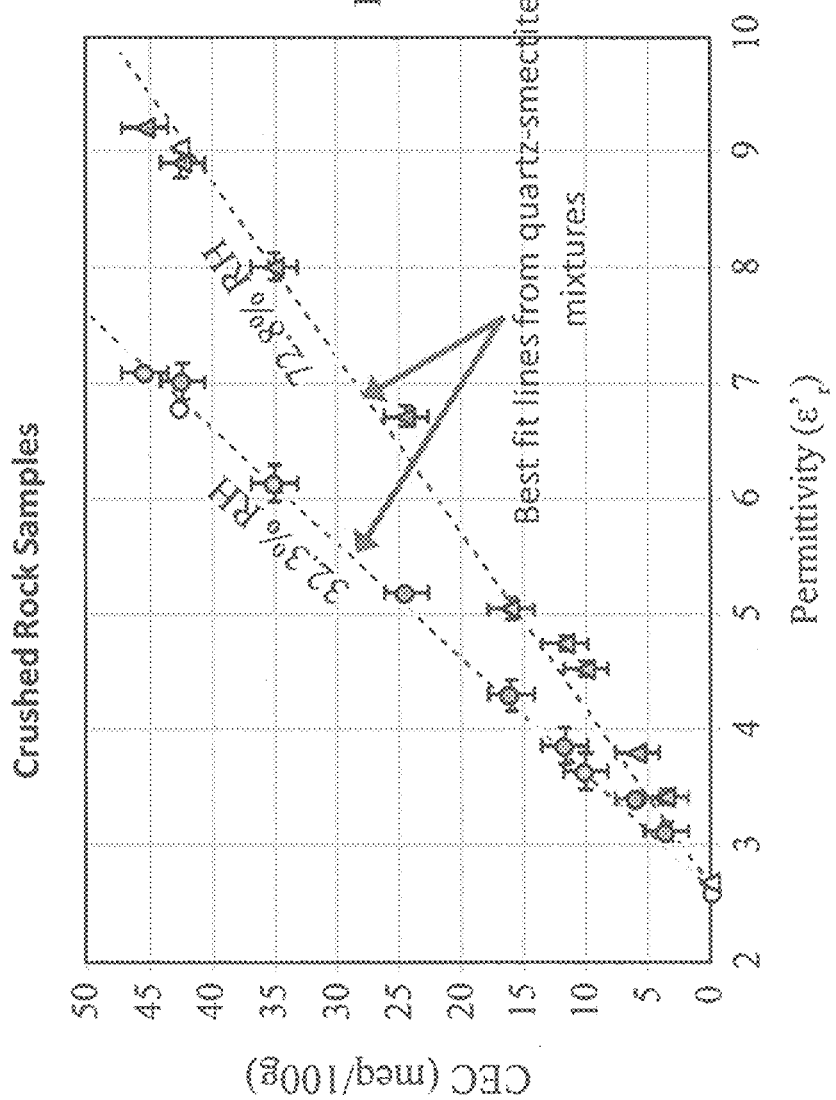
FIG. 7 illustrates permittivity vs. measured CEC for the crushed rock samples (filled shapes) at 32.3% and 72.8% RH. Dashed lines are the best-fit lines defined by the quartz-smectite mixtures (open shapes) shown in FIG. 5.

The slope values ($CEC/\varepsilon'_r$) shown in FIG. 5 are plotted against their corresponding RH value in FIG. 6 to establishes the relationship between CEC and permittivity as a function of RH from 8% to 72% at 21° C. It becomes apparent that there are three linearly-related regions defined by the intersection of best fit lines at low (<18%), moderate (18-35%), and high (>35%) RH conditions. The best fit lines for these regions have $R^2$ values >0.98. It should be noted that a single curve approach to fitting the data was evaluated, however, due to the sharp change in slope between the mid and high RH regions, simple exponential and power decay equations were not adequate to fit the full dataset. It should also be addressed that the mid-range RH best fit line is defined by only two data points, and it is recognize that more data points would make a stronger case for the following interpretations. Despite the limited number of data points, errors ($CEC_{measured} - CEC_{calculated}$) of calculated CEC values are reasonable, suggesting that the addition of more data points would not change the correlations.

The three RH dependent linear curves (FIG. 6) provide equations that allow for $S_{RH}$ to be calculated using Equation (3).

$$S_{RH} = S_{l,m,h}(RH) + c_{l,m,h} \qquad \text{Equation (3)}$$

The parameters to solve for $S_{RH}$ are $S_{l,m,h}$ and $c_{l,m,h}$ which are the slope and y-intercept values provided in the table embedded in FIG. 6; l, m, and h stand for low-, mid-, and high-RH conditions. Their respective values should be substituted into Equation (3) depending on the RH recorded during permittivity data collection. Now that $S_{RH}$ can be calculated, $c_{RH}$ can be calculated using Equation (2). This is possible because the best-fit lines for each RH meet at 2.5 $\varepsilon'_r$, CEC=0 (see FIG. 5) thus leaving a simple equation to solve for $c_{RH}$ (Equation (4)).

$$c_{RH} = -S_{RH}(2.5) \qquad \text{Equation (4)}$$

3.1 Dielectric Results—3.1.2 Crushed rock samples: Dielectric analysis results on the crushed rock samples at 32.3% and 72.8% RH are plotted in FIG. 7. These data are shown together with the lower CEC quartz-smectite mixture data from the same RH conditions where the dashed lines are the same as the best-fit lines shown in FIG. 5. There is good agreement between the crushed rock data and quartz-smectite mixtures despite significant differences in particle size, porosity, and mineralogy—specifically clay speciation (FIG. 2A, 2B).

Figure 8:
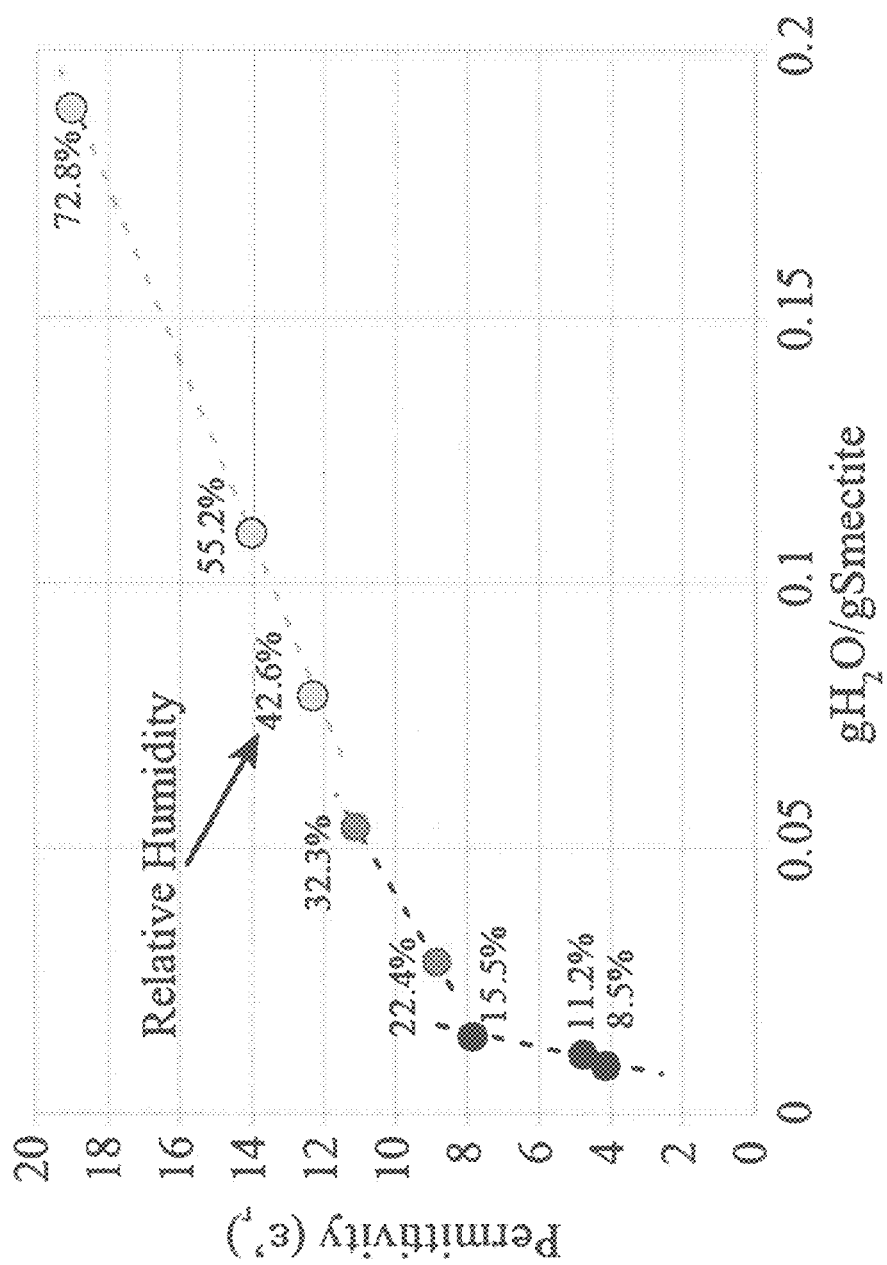
FIG. 8 illustrates permittivity vs. amount of water adsorbed by pure smectite at specific RH conditions (% next to circles) that match those investigated in this study.

3.2 Water-Vapor Adsorption Results: Water vapor adsorption results provide information about the amounts of adsorbed water and rate of adsorption that ultimately control the permittivity. We do not show the rate of water adsorption data from these experiments, however this component of the data provided valuable information regarding how quickly high CEC samples adsorb $H_2O$, thus altering the way we collected data and treated samples prior to, and during dielectric analysis. FIG. 8 shows the relationship between permittivity and the amount of adsorbed $H_2O$ by smectite as a function of RH. At low RH conditions, the steep slope of the best-fit line establishes that the addition of relatively small amounts of water vapor to dry smectite has a very strong impact on the dielectric response of the material. This strong dielectric response lessens by an order of magnitude around 18% RH which, unsurprisingly, corresponds to the boundary between the low- and mid-RH regions identified in FIG. 6.

3.3 Method Validation: Using Equations (2)-(4), CEC was calculated for the quartz-smectite and crushed rock samples to evaluate the method presented in the paper. There was a consistent positive offset of the calculated CEC from the lab-measured CEC of ~4 meq/100 g. This correction factor (C) is applied to Equation (2), yielding Equation (5). The source of this error is worth investigation though it is not evaluated herein.

$$CEC = S_{RH}\varepsilon'_r + c_{RH} + C \qquad \text{Equation (5)}$$

Figure 9:
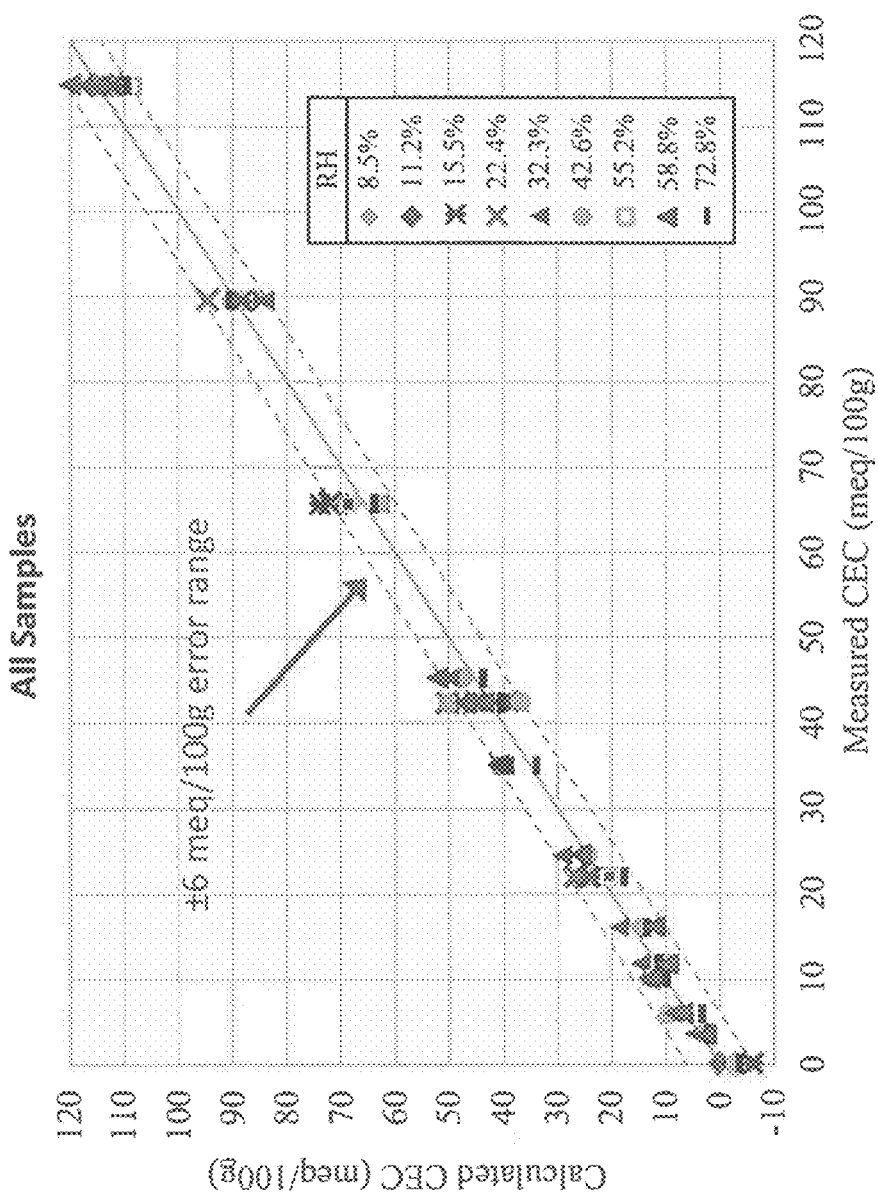
FIG. 9 illustrates calculated CEC using Equation 5 vs. the laboratory measured CEC for the crushed rock samples (max. CEC of 45 meq/100 g) and quartz:smectite standards. Solid grey line is the 1:1 line, dashed grey lines define the ±6 meq/100 g error field.
Figure 10:
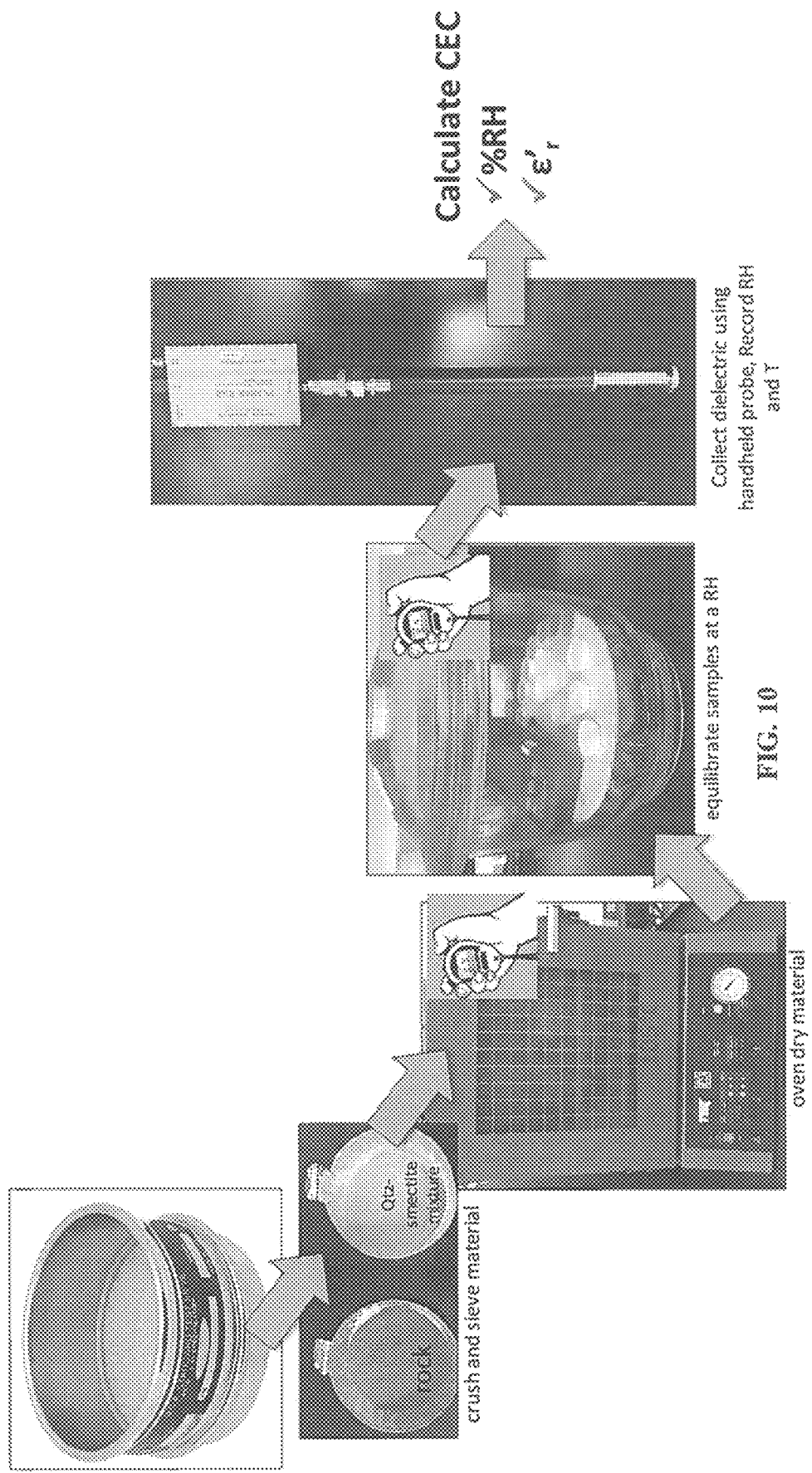
FIG. 10 illustrates one embodiment of generating one or more equations and using the one or more equations consistent with the present disclosure.

Adjusted calculated CEC values using Equation (5) are plotted against laboratory measured CEC in FIG. 9. There is good agreement within ±6 meq/100 g between calculated and measured CEC for all samples (quartz-smectite and crushed rock samples) from 8-73% RH.

4.1 Method application and limitations: The portable CEC analysis technique discussed herein that does not require significant sample preparation or the use of chemicals. Creating a method to quickly generate CEC data would be particularly useful for drilling engineers and geologists to assess changes in the swelling potential of rocks being drilled and account for potentially impacted processes in real-time. The method presented in these sections provides a procedure and set of equations for a CEC-proxy tool that can be developed for specific laboratory/field conditions where RH (and temperature) conditions are often not constant.

Identified limitations of this technique include: 1) Specific values provided for $S_{l,m,h}$, $c_{l,m,h}$, and C are only applicable if collecting data at the same temperature (around 21° C. in this study) and frequency (120 MHz). Permittivity measurements in the high-frequency range are sensitive to changes in temperature, thus operating conditions outside of this may require new calibration curves similar to what are shown in FIG. 5 such that new values can be calculated for $S_{l,m,h}$, $c_{l,m,h}$, and C. However, once established, the analyses and CEC calculations are straight forward and fast to obtain. 2) This study attempted to use a wide range of rock types to validate the method (FIG. 2A, 2B) however, there are some minerals/phases that were not covered and may not be suitable for this method. These include Mg-dominant smectite, certain zeolites, opal varieties, significant amounts of solid organic matter, and grain coating liquid hydrocarbon. Other parameters that showed surprisingly little to no impact on the dielectric response were porosity, particle size, and compositional variations of illite-smectite (e.g. exchangeable cations and associated variations in layer charge). 3) This method has been validated for use in RH conditions ranging from 8-73% RH. At very low RH condition, there will not be enough $H_2O$ in the system to be conducive to dielectric analysis. At very high RH conditions (>~75%) it is well documented that capillary condensation in porous media dominates water sorption mechanisms and is a phenomenon mostly independent of CEC. Both scenarios would significantly complicate the relationship between RH, CEC, and permittivity.

Results of this study provide a set of equations and methodology that allow CEC to be calculated from the real part of the complex permittivity. To do this, a series of equations were developed to determine the RH dependent relationship between CEC and permittivity such that if the RH is known and the permittivity measured, bulk CEC can be calculated. Approximate error for the CEC calculation using these equations is ±6 meq/100 g, which for the purposes of discriminating rocks that will have issues due to clay swelling, is acceptable.

The handheld tool used for dielectric analyses is portable and relatively easy to set up and calibrate. As illustrated, sample preparation only requires hand grinding the rock to pass through a 40-mesh sieve and oven drying the sample to remove any water and liquid hydrocarbons, if present, and equilibrating the sample to a single RH for at least 24 hours. This tool and set of equations are a portable and easy to use option for calculating CEC in lieu of traditional laboratory-based methods.

To summarize, one or more equations may be previously generated using mineral mixtures (e.g., quartz and smectite mixtures), and then the one or more equations may be utilized to determine the cation exchange capacity of a new rock sample. For example, the one or more equations may be previously generated in association with a frequency and a temperature, and then the one or more equations may be utilized to determine the cation exchange capacity of the new rock sample at the frequency and the temperature. If the temperature and/or the frequency associated with the new rock sample are different than the temperature and/or the frequency associated with the one or more equations, then the one or more equations may be regenerated for the new frequency and/or the new temperature. For example, new equations may be derived if analyzing rock samples at a temperature different from 21° C. The one or more equations that were regenerated at the new frequency and/or the new temperature may then be utilized to determine the cation exchange capacity for the new rock sample at the new frequency and/or the new temperature. The new rock sample undergoes less preparation to determine the cation exchange capacity as compared to conventional methodologies. For example, the handheld tool used for dielectric analyses is portable and relatively easy to set up and calibrate. Sample preparation involved hand grinding the rock to pass through a 40-mesh sieve and oven drying the sample to remove any water and liquid hydrocarbons, if present, and equilibrating the sample to a single RH for at least 24 hours.

Indeed, measuring the CEC of a rock is typically laborious, and depending on the method used, requires saturation and extraction steps, the use of multiple chemicals, titration, and spectroscopic analysis. This study uses the petrophysical link between clays and relative permittivity ($\varepsilon'_r$) and outlines a work flow and set of equations that allow for bulk rock CEC to be calculated from permittivity measurements of crushed rock using a handheld dielectric probe. A series of quartz-smectite mineral mixtures were prepared and high-frequency (80 MHz-1.4 GHz) dielectric measurements collected at six relative humidity (RH) conditions ranging from 8-75%. For each RH data set, a strong linear relationship ($R^2 \geq 0.98$) exists between permittivity at 120 MHz and the lab-measured CEC of the mineral mixtures. The equations from these calibration curves were used to derive 3 RH-dependent equations. The method was validated on a variety of crushed sedimentary rocks and differences between the calculated values from this study and the lab-measured CECs range between +/−6 meq/100 g. These results demonstrate that dielectric permittivity measurements can be used as a CEC-proxy and is a faster and flexible alternative to laboratory-based CEC analysis. FIGS. 1B-10 correspond to this discussion.

Returning to FIG. 1A, those of ordinary skill in the art will appreciate that various modification may be made to the method 100. As an example, optionally, at 120, the method 100 may also include breaking up the rock sample prior to performing the dielectric permittivity measurement on the rock sample. In one embodiment, the rock sample may be broken up into rock particles by grinding. The grinding may be performed by hand with a mortar and pestle. However, the rock sample may be broken up into rock particles using practically any technique known to those of ordinary skill in the art.

As another example, optionally, at 125, the method 100 may also include passing the rock sample through a mesh sieve prior to performing the dielectric permittivity measurement on the rock sample. In one embodiment, the mesh sieve comprises a 40 mesh sieve (0.42 mm). The mesh sieve may be a different size in another embodiment. However, the rock sample may be broken up into rock particles using practically any technique known to those of ordinary skill in the art. For example, the rock particles from 120 may be passed through a mesh sieve, such as the 40 mesh sieve, at 125.

As another example, optionally, at 130, the method 100 may also include dehydrating the rock sample prior to equilibrating the rock sample to the relative humidity. The rock sample may be dehydrated in an oven to remove fluid, such as water and liquid hydrocarbons, from the rock sample. For example, the rock particles that passed through the mesh sieve at 125 may be dehydrated at 130 prior to equilibrating the rock particles to the relative humidity at 105.

In one embodiment, dehydrating the rock sample comprises heating the rock sample to at least 100 Degrees Celsius (e.g., at least 100 Degrees Celsius, at least 101 Degrees Celsius, at least 102 Degrees Celsius, at least 103 Degrees Celsius, at least 104 Degrees Celsius, at least 105 Degrees Celsius, at least 106 Degrees Celsius, at least 107 Degrees Celsius, at least 108 Degrees Celsius, at least 109 Degrees Celsius, at least 110 Degrees Celsius, at least 115 Degrees Celsius, at least 120 Degrees Celsius, at least 125 Degrees Celsius, at least 130 Degrees Celsius, at least 135 Degrees Celsius, at least 140 Degrees Celsius, at least 145 Degrees Celsius, at least 150 Degrees Celsius, at least 175 Degrees Celsius, or at least 200 Degrees Celsius). In some embodiments, dehydrating the rock sample comprises heating the rock sample to 200 Degrees Celsius or less (e.g., 175 Degrees Celsius or less, 150 Degrees Celsius or less, 145 Degrees Celsius or less, 140 Degrees Celsius or less, 135 Degrees Celsius or less, 130 Degrees Celsius or less, 125 Degrees Celsius or less, 120 Degrees Celsius or less, 115 Degrees Celsius or less, 110 Degrees Celsius or less, 109 Degrees Celsius or less, 108 Degrees Celsius or less, 107 Degrees Celsius or less, or 106 Degrees Celsius or less. Dehydrating the rock sample comprises heating the rock sample to an amount ranging from any of the minimum values described above to any of the maximum values described above. For example, in some embodiments, dehydrating the rock sample comprises heating the rock sample to between 105 Degrees Celsius and 200 Degrees Celsius (e.g., between 105 Degrees Celsius and 110 Degrees Celsius, between 105 Degrees Celsius and 115 Degrees Celsius, between 105 Degrees Celsius and 125 Degrees Celsius, between 105 Degrees Celsius and 150 Degrees Celsius, or between 105 Degrees Celsius and 175 Degrees Celsius). In one embodiment, dehydrating the rock sample comprises heating the rock sample to at least about 105 Degrees Celsius, such as ±10 percent of 105 Degrees Celsius.

In some embodiments, 120, 125, and 130 of the method 100 may be performed. In some embodiments, dehydrating may be avoided for rock samples (or rock particles) that are unlikely to contain fluid, such as rock samples (or rock particles) from a desert environment.

As another example, optionally, at 135, the method 100 may also include determining a smectite content of a dioctahedral clay group in the rock sample based on the determined cation exchange capacity. For example, the smectite content may be determined using Equation (1), which is illustrated below, using the determined cation exchange capacity from 115. The term $CEC_{meas}$ is the cation exchange capacity that was determined at 115. Equation (1) was discussed hereinabove.

$$\% \, S \, in \, I-S = \frac{CEC_{meas} - CEC_I}{CEC_S - CEC_I} \times 100 \qquad \text{Equation (1)}$$

As another example, optionally, at 140, the method 100 may also include determining a second cation exchange capacity for a second rock sample. The second rock sample is from a same reservoir as the rock sample. As another example, optionally, at 145, the method 100 includes determining a second cation exchange capacity for a second rock sample at a point in time later than when the cation exchange capacity for the rock sample was determined. In one embodiment, the second cation exchange capacity is determined at least 1 hour later (e.g., 3 hours later, 6 hours later, 12 hours later, 24 hours later, 36 hours later, 48 hours later, 7 days later, 30 days later, 3 months later, 6 months later, 12 months later, or 24 months later). In some embodiments, the second cation exchange capacity is determined 24 months or less later (e.g., 24 months or less later, 12 months or less later, 6 months or less later, 3 months or less later, 30 days or less later, 7 days or less later, 48 hours or less later, 36 hours or less later, 24 hours or less later, 12 hours or less later, 6 hours or less later, 3 hours or less later). The second cation exchange capacity is determined at a later point in time such as an amount ranging from any of the minimum values described above to any of the maximum values described above. For example, in some embodiments, the second cation exchange capacity is determined between 1 hour and 24 months later (e.g., between 1 hour and 12 hours later, between 1 hour and 24 hours later, between 1 hour and 48 hours later, between 1 day and 7 days later, between 30 days and 90 days later, between 30 days and 12 months later, or between 6 months and 18 months later).

In one embodiment, the two cation exchange capacities may be determined for two rock samples from the same reservoir before and after a reservoir treatment on the same reservoir. The two cation exchange capacity values may be compared to determine the effect of the reservoir treatment on the same reservoir. The reservoir treatment may be an EOR operation. A person of ordinary skill in the art will appreciate that there may be other reasons to determine two cation exchange capacities.

Figure 11:
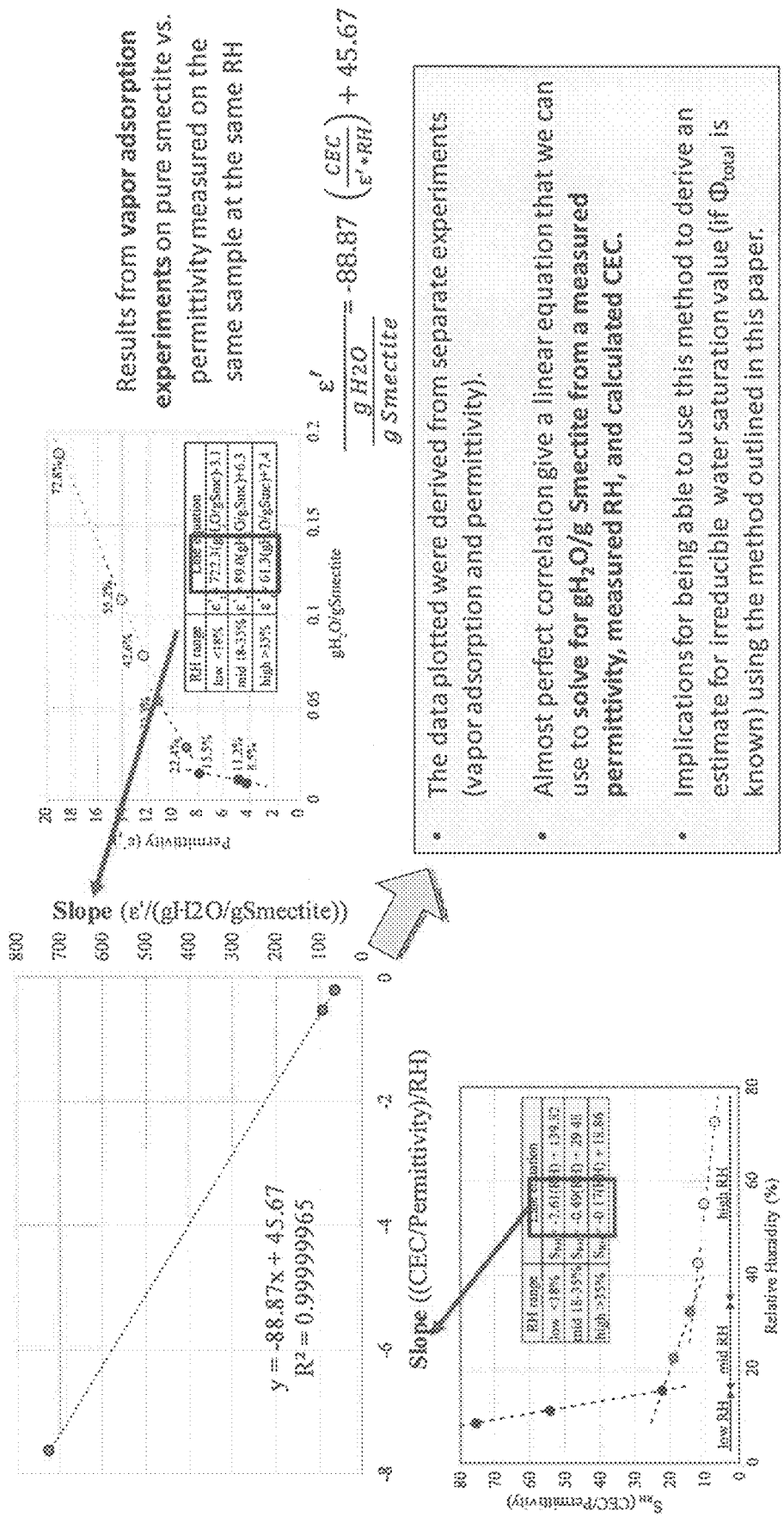
FIG. 11 illustrates one embodiment of determining a value associated with water saturation for the rock sample.

As another example, optionally, at 150, the method 100 may also include determining a value associated with water saturation for the rock sample. The term "water saturation" herein refers to a volume of water adsorbed on mineral surfaces at any given relative humidity. In one embodiment, the value associated with water saturation for the rock sample comprises an irreducible water saturation value. For example, water adsorption data from pure smectite indicates that a water saturation value similar to Swirr may be determined if the porosity is known. In one embodiment, the value associated with water saturation for the rock sample comprises clay-bound water saturation value. In one embodiment, the value associated with water saturation for the rock sample is determined based on the measured dielectric permittivity measurement, the relative humidity, the cation exchange capacity, and a porosity of the rock sample. FIG. 11 illustrates an embodiment of determining a value associated with water saturation for the rock sample.

4.2 Clay-water interaction and dielectric response: The physiochemical processes governing the relationship between $S_{RH}$ and RH as shown in FIG. 6 may be useful in determining a value associated with water saturation for the rock sample. At RH conditions below ~18%, there is a strong dielectric response to very little $H_2O$ in the environment and above this the response is not as strong relative to the ever-increasing amounts of $H_2O$ adsorbed by smectite. In the case of pure smectite, the water adsorption behavior in this RH region is largely controlled by the size and valance of the exchangeable cation in the TOT (tetrahedral-octahedral-tetrahedral) interlayers and their corresponding hydration enthalpies ($Mg^{2+}>>Ca^{2+}>Na^+>K^+$). Numerous studies have used X-ray diffraction to describe smectite swelling behavior through tracking the changes in the basal d-spacing of different smectite species at a range of RH conditions. These results consistently show that interlayer expansion for $K^+$, $Na^+$, $Ca^{2+}$, and $Mg^{2+}$-exchanged smectite typically starts at >20%, ~20% RH, ~20% RH, ~10% RH, and <10% RH, respectively. The smectite (Tsukinuno montmorillonite) used in this study is $Na^{2+}$-dominant (>75%) with measurable amounts of $Ca^{2+}$ and $Mg^{2+}$ (Ca>Mg). Based on this information, most of the interlayer expansion via $H_2O$ adsorption starts around 20% RH which corresponds to the drastic change in the $S_{RH}$-RH relationship identified in this study at 18% RH. It follows that at RH conditions lower than ~20%, the large changes in permittivity are possibly due to $H_2O$ adsorption on high CEC mineral surfaces and edges. As RH increases and smectite interlayer adsorption begins to dominate, the dielectric response decreases relative to the increased adsorption of interlayer $H_2O$.

At higher RH values, a more subtle change in the relationship between $S_{RH}$ and RH occurs at ~35% RH, and defines the boundary between the mid- to high-RH ranges shown in FIG. 6. This RH value corresponds to published data that mark the prevalence of monolayer adsorption of $H_2O$ around cation/charged sites in Na-montmorillonite similar to the smectite standard used in this study. This loose interpretation of the data from this study may require further evaluation, however if a physiochemical-based explanation for the empirical relationships identified between RH, CEC and dielectric response can be provided, it would make an even stronger case for the use of dielectric permittivity as a proxy for CEC.

In short, a person of ordinary skill in the art will appreciate that various modifications are possible and the inventive concepts are not limited to the embodiments provided herein. For example, in a first embodiment, the method 100 may include 105, 110, and 115. In a second embodiment, the method 100 may include 105, 110, 115, and 135. In a third embodiment, the method 100 may include 105, 110, 115, and 140. In a fourth embodiment, the method 100 may include 105, 110, 115, 140, and 145. In a fifth embodiment, the method 100 may include 120, 125, 130, 105, 110, and 115. In a sixth embodiment, the method 100 may include 120, 125, 130, 105, 110, 115, and 135. In a seventh embodiment, the method 100 may include 120, 125, 130, 105, 110, 115, and 140. In an eighth embodiment, the method 100 may include 120, 125, 130, 105, 110, 115, 140, and 145 (see FIG. 1A). Any of these eight embodiments may even include 150. A person of ordinary skill in the art will also appreciate that other uses for the determined cation exchange capacity are possible.

Figure 12:
FIG. 12 illustrates a flowchart of another embodiment of a method of determining a cation exchange capacity of a rock sample consistent with the present disclosure.

Turning to FIG. 12, this figure illustrates another embodiment of a method 200 of determining a cation exchange capacity of a rock sample. FIG. 12 includes various steps, such as optional steps, discussed in the context of FIG. 1A.

At 205, the method 200 includes receiving a dielectric permittivity measurement on the rock sample. For example, the dielectric permittivity measurement on the rock sample from 110 of the method 100 may be received. For example, the dielectric permittivity measurement on the rock sample may be previously taken at 110 and it may be received at 205.

At 210, the method 200 includes determining a cation exchange capacity for the rock sample based on the dielectric permittivity measurement of the rock sample and a relationship between cation exchange capacity and dielectric permittivity measurements for mineral mixtures corresponding to a range of cation exchange capacity values. In one embodiment, the mineral mixture comprises quartz-smectite ratios. For example, the relationships discussed hereinabove in the EQUATION GENERATION section may be utilized at 210.

In one embodiment, the dielectric permittivity measurement for the rock sample is performed at a temperature that is consistent with the dielectric permittivity measurements of the mineral mixture. Regarding the term "consistent", it may depend on the embodiment. Regarding "consistent," in one embodiment, the temperature used with the dielectric permittivity measurement for the rock sample is the same temperature used with the dielectric permittivity measurements of the mineral mixture, for example, both temperatures are 21 Degrees Celsius. The same temperature may lead to more accurate cation exchange capacities.

However, regarding "consistent," in one embodiment, the temperature used with the dielectric permittivity measurement for the rock sample is ±10 percent of the temperature used with the dielectric permittivity measurements of the mineral mixture. Regarding "consistent," in one embodiment, the temperature range used with the dielectric permittivity measurement for the rock sample is the same temperature range used with the dielectric permittivity measurements of the mineral mixture. These similar temperatures may lead to less accurate cation exchange capacities that may still be utilized in some contexts.

In one embodiment, the dielectric permittivity measurement for the rock sample is performed at a frequency that is consistent with the dielectric permittivity measurements of the mineral mixture. Regarding the term "consistent", it may depend on the embodiment. Regarding "consistent," in one embodiment, the frequency used with the dielectric permittivity measurement for the rock sample is the same frequency used with the dielectric permittivity measurements of the mineral mixture, for example, both frequencies are 120 MHz. The same frequency may lead to more accurate cation exchange capacities.

However, regarding "consistent," in one embodiment, the frequency used with the dielectric permittivity measurement for the rock sample is ±10 percent of the frequency used with the dielectric permittivity measurements of the mineral mixture. Regarding "consistent," in one embodiment, the frequency range used with the dielectric permittivity measurement for the rock sample is the same frequency range used with the dielectric permittivity measurements of the mineral mixture. These similar frequencies may lead to less accurate cation exchange capacities that may still be utilized in some contexts.

In one embodiment, the dielectric permittivity measurement for the rock sample is performed at a relative humidity that is consistent with the dielectric permittivity measurements of the mineral mixture. Regarding the term "consistent", it may depend on the embodiment. Regarding "consistent," in one embodiment, the relative humidity used with the dielectric permittivity measurement for the rock sample is the same relative humidity used with the dielectric permittivity measurements of the mineral mixture. The same relative humidity may lead to more accurate cation exchange capacities.

However, regarding "consistent," in one embodiment, the relative humidity used with the dielectric permittivity measurement for the rock sample is +10 percent of the relative humidity used with the dielectric permittivity measurements of the mineral mixture. Regarding "consistent," in one embodiment, the relative humidity range used with the dielectric permittivity measurement for the rock sample is the same relative humidity range used with the dielectric permittivity measurements of the mineral mixture, such as relative humidity range 8%-75%. These similar relative humidities may not adversely impact the accuracy of the cation exchange capacities that are determined. Indeed, in some embodiments, the same frequencies and/or the same temperatures (and not the same relative humidities) may impact the accuracy of the cation exchange capacities that are determined.

The methods of the appended claims are not limited in scope by the specific methods described herein, which are intended as illustrations of a few aspects of the claims. Any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps or elements may be explicitly mentioned herein, however, other combinations of steps or elements are included, even though not explicitly stated.

The invention claimed is:

1. A method of determining a cation exchange capacity of a rock sample, the method comprising:
    preparing a rock sample to equilibrate to a relative humidity, wherein preparing the rock sample comprises crushing the rock sample into rock particles, passing the rock particles through a mesh sieve, and dehydrating the rock particles;
    equilibrating the rock sample to the relative humidity;
    performing a dielectric permittivity measurement on the rock sample at the relative humidity; and
    determining a cation exchange capacity of the rock sample based on the dielectric permittivity measurement.

2. The method of claim 1, wherein the rock sample is equilibrated to the relative humidity of between about 8% and about 75%.

3. The method of claim 1, wherein the dielectric permittivity measurement on the rock sample is performed at a frequency between about 80 megahertz and about 600 megahertz.

4. The method of claim 1, wherein the rock sample comprises a drill cutting, a core sample, a soil sample, an outcrop sample, a mudcake sample, or any combination thereof.

5. The method of claim 1, further comprising determining a smectite content of a dioctahedral clay group in the rock sample based on the determined cation exchange capacity.

6. The method of claim 1, further comprising maintaining the rock sample at a constant temperature while performing the dielectric permittivity measurement.

7. The method of claim 1, wherein the cation exchange capacity for the rock sample is determined using the following equation:

$$CEC = S_{RH}\varepsilon'_r + c_{RH}$$

where $\varepsilon'_r$ represents the dielectric permittivity measurement on the rock sample, $S_{RH}$ represents a slope for a linear relationship between the cation exchange capacity and the dielectric permittivity measurement as a function of relative humidity, and $c_{RH}$ represents a y-intercept constant for the linear relationship between the cation exchange capacity and the dielectric permittivity measurement as the function of relative humidity.

8. The method of claim 7, wherein $S_{RH}$ is segmented into a plurality of regions that each span a range of relative humidities, the regions being segmented by changes in a slope of a linear relationship between $S_{RH}$ and relative humidity.

9. The method of claim 7, wherein $S_{RH}$ and $c_{RH}$ are determined based on a plot of cation exchange capacities and dielectric permittivity measurements as a function of relative humidity for mineral mixtures corresponding to a range of cation exchange capacity values.

10. The method of claim 7, wherein $S_{RH}$ and $c_{RH}$ are determined based on a plot of cation exchange capacities and dielectric permittivity measurements as a function of relative humidity for known quartz-smectite ratios.

11. The method of claim 10, wherein a desiccant is used to obtain a plurality of relative humidities for the known quartz-smectite ratios.

12. The method of claim 1, wherein a correction factor is applied to the cation exchange capacity calculated for the rock sample.

13. The method of claim 1, wherein the cation exchange capacity for the rock sample is determined using the following equation:

$$CEC = S_{RH}\varepsilon'_r + c_{RH} + C$$

where $\varepsilon'_r$ represents the dielectric permittivity measurement on the rock sample, $S_{RH}$ represents a slope for a linear relationship between the cation exchange capacity and the dielectric permittivity measurement as a function of relative humidity, $c_{RH}$ represents a y-intercept constant for the linear relationship between the cation exchange capacity and the dielectric permittivity measurement as the function of relative humidity, and C represents a correction factor applied to the cation exchange capacity.

14. The method of claim 1, further comprising determining a value associated with water saturation for the rock sample.

15. The method of claim 14, wherein the value associated with water saturation for the rock sample comprises an irreducible water saturation value.

16. The method of claim 1, further comprising determining a second cation exchange capacity for a second rock sample, wherein the second rock sample is from a same reservoir as the rock sample.

17. The method of claim 1, further comprising determining a second cation exchange capacity for a second rock sample at a point in time later than when the cation exchange capacity for the rock sample was determined.

18. A method of determining a cation exchange capacity of a rock sample, the method comprising:
   receiving a dielectric permittivity measurement for a rock sample, wherein the rock sample was prepared to equilibrate to a relative humidity by crushing the rock sample into rock particles, passing the rock particles through a mesh sieve, and dehydrating the rock particles, and wherein the rock sample was equilibrated to the relative humidity, and wherein the dielectric permittivity measurement was performed on the rock sample at the relative humidity; and
   determining a cation exchange capacity for the rock sample based on the dielectric permittivity measurement of the rock sample and a relationship between cation exchange capacity and dielectric permittivity measurements for mineral mixtures corresponding to a range of cation exchange capacity values.

* * * * *